US011254973B2

(12) United States Patent
Jones et al.

(10) Patent No.: US 11,254,973 B2
(45) Date of Patent: Feb. 22, 2022

(54) SYSTEMS AND METHODS FOR SINGLE MOLECULE QUANTIFICATION

(71) Applicant: Invitae Corporation, San Francisco, CA (US)

(72) Inventors: Hywel Bowden Jones, San Francisco, CA (US); Andrea Lynn McEvoy, San Francisco, CA (US)

(73) Assignee: Invitae Corporation, San Francisco, CA (US)

( * ) Notice: Subject to any disclaimer, the term of this patent is extended or adjusted under 35 U.S.C. 154(b) by 372 days.

(21) Appl. No.: 16/329,816

(22) PCT Filed: Sep. 1, 2017

(86) PCT No.: PCT/US2017/049823
§ 371 (c)(1),
(2) Date: Mar. 1, 2019

(87) PCT Pub. No.: WO2018/045270
PCT Pub. Date: Mar. 8, 2018

(65) Prior Publication Data
US 2019/0241940 A1 Aug. 8, 2019

Related U.S. Application Data

(60) Provisional application No. 62/383,378, filed on Sep. 2, 2016.

(51) Int. Cl.
*C12Q 1/6837* (2018.01)
*C12Q 1/6818* (2018.01)
*C12Q 1/686* (2018.01)
*C12Q 1/6876* (2018.01)
*G06T 7/11* (2017.01)
*G06K 9/00* (2022.01)
*G06K 9/46* (2006.01)
*G16B 40/00* (2019.01)
*G16B 20/00* (2019.01)
*G16B 30/00* (2019.01)

(52) U.S. Cl.
CPC .......... *C12Q 1/6837* (2013.01); *C12Q 1/686* (2013.01); *C12Q 1/6818* (2013.01); *C12Q 1/6876* (2013.01); *G06K 9/00127* (2013.01); *G06K 9/4647* (2013.01); *G06T 7/11* (2017.01); *G06T 2207/30072* (2013.01); *G16B 20/00* (2019.02); *G16B 30/00* (2019.02); *G16B 40/00* (2019.02)

(58) Field of Classification Search
CPC .... C12Q 1/6837; C12Q 1/6818; C12Q 1/686; C12Q 1/6876; G16B 40/00; G16B 20/00; G16B 30/00; G06K 2209/07; G06T 7/11; G06T 2207/30072
See application file for complete search history.

(56) References Cited

U.S. PATENT DOCUMENTS

| 10,515,447 | B2* | 12/2019 | Bolstad | G06T 5/009 |
|---|---|---|---|---|
| 2005/0244863 | A1* | 11/2005 | Mir | B01J 19/0046 |
| | | | | 435/6.11 |
| 2005/0266417 | A1* | 12/2005 | Barany | C12Q 1/6827 |
| | | | | 435/6.12 |
| 2007/0213939 | A1 | 9/2007 | Liew et al. | |
| 2014/0186827 | A1* | 7/2014 | Pieprzyk | C12Q 1/6855 |
| | | | | 435/6.11 |
| 2015/0167077 | A1 | 6/2015 | Fehr et al. | |

FOREIGN PATENT DOCUMENTS

WO  2010/084381 A1  7/2010

OTHER PUBLICATIONS

International Search Report issued in corresponding International Patent Application No. PCT/US2017/049823 dated Dec. 27, 2017.
Written Opinion issued in corresponding International Patent Application No. PCT/US2017/049823 dated Dec. 27, 2017.
Extended European Search Report issued in corresponding European Patent Application No. 17847615.6 dated Mar. 19, 2020.
Karim et al., "A Review of Image Analysis Techniques for Gene Spot Identification in cDNA Microarray Images", INCIT, Jun. 21, 2011, pp. 36-41.
Trcek et al., mRNA Quantification Using Single-Molecular FISH in *Drosophila* Embryos, Nature Protocols, Jun. 8, 2016, 12:1326-1348.

* cited by examiner

*Primary Examiner* — David C Thomas
(74) *Attorney, Agent, or Firm* — Wolf, Greenfield & Sacks, P.C.

(57) ABSTRACT

A method for quantifying labels on a substrate is performed by an electronic device with one or more processors and memory. The method includes obtaining digital data corresponding to a multi-dimensional measurement over the substrate; identifying a first set of sub-portions of the digital data; and, for a respective sub-portion of the first set of sub-portions of the digital data: increasing a quantity of labels, and subtracting a reference signal distribution from the respective sub-portion to obtain subtracted sub-portion data. The method also includes obtaining subtracted digital data. The subtracted digital data includes the subtracted sub-portion data for the respective sub-portion. The method further includes identifying a second set of one or more sub-portions of the subtracted digital data; and, for a respective sub-portion of the second set of one or more sub-portions of the subtracted digital data, increasing a quantity of labels.

14 Claims, 17 Drawing Sheets

356

| 370-1 | 370-2 | 370-3 | ••• | 370-N+8 |
| 370-4 | 370-5 | 370-6 | ••• | 370-N+7 |
| 370-7 | 370-8 | 370-9 | ••• | 370-N+6 |
| ⋮ | ⋮ | ⋮ | ⋱ | 370-N+5 |
| 370-N | 370-N+1 | 370-N+2 | 370-N+3 | 370-N+4 |

602 Obtain digital data corresponding to a multi-dimensional measurement over the substrate > 604 Obtaining the digital data of the substrate includes obtaining digital data of labels on the substrate. The labels are not immersed in a liquid solution.

606 Identify a first set of sub-portions of the digital data. Each sub-portion of the first set of sub-portions is a subset, less than all, of the entire digital data and includes signal of one or more labels.

> 608 The first set of sub-portions includes two or more sub-portions. The two or more sub-portions in the first set are not contiguous.

610 For a respective sub-portion of the first set of sub-portions of the digital data: increase a quantity of labels; and subtract a reference signal distribution from the respective sub-portion to obtain subtracted sub-portion data.

> 612 Subtracting the reference signal distribution from the respective sub-portion includes: identifying a location, within the respective sub-portion, with a peak signal intensity; aligning the reference signal distribution to the location with the peak signal intensity; and subtracting the reference signal distribution, aligned to the location with the peak signal intensity, from the respective sub-portion.

> 614 The reference signal distribution corresponds to a point spread function of a single signal molecule (A)

702 Obtain digital data representing a series of intensity values of one or more labels within a particular region over a period of time. The series of intensity values of one or more labels includes intensity values of the one or more labels at respective time frames within the period of time. The series of intensity values of one or more labels includes a first group of intensity values and a second group of intensity values.

704 The first group of intensity values corresponds to a first range of intensity values. The second group of intensity values corresponds to a second range of intensity values that does not overlap with the first range of intensity values.

706 The first intensity value is an average of the first group of intensity values. The second intensity value is an average of the second group of intensity values.

708 Determine from the digital data a first intensity value that represents the first group of intensity values and a second intensity value that represents the second group of intensity values and is distinct from the first intensity value

710 Determining the first intensity value and the second intensity value includes separating the series of intensity values into at least the first group of intensity values and the second group of intensity values

712 Replace the second group of intensity values with the first intensity value

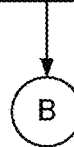

FIGURE 7A

714 Quantify a number of the one or more labels, represented by the digital data, based on at least the first intensity value

716 Quantifying the number of the one or more labels includes quantifying the number of the one or more labels based on at least the first intensity value and another intensity value

718 Obtain a series of adjusted intensity values by subtracting the second intensity value from the series of intensity values. Quantifying the number of the one or more labels includes quantifying the number of the one or more labels based on the series of adjusted intensity values.

720 Determine a total intensity value from the series of intensity values; and quantify the number of the one or more labels based on at least the total intensity value

722 Quantify the number of the one or more labels as one based on a determination that the series of intensity values consists of the first group of intensity values and the second group of intensity values

724 The series of intensity values of one or more labels also includes a third group of intensity values that is represented by a third intensity value that is distinct from the first intensity value and the second intensity value. Quantify the number of the one or more labels as two based on a determination that the series of intensity values consist of the first group of intensity values, the second group of intensity values, and the third group of intensity values.

726 The series of intensity values of one or more labels also includes one or more additional groups of intensity values, each group of intensity values represented by a respective intensity value that is distinct from any intensity value that represents any other group of intensity values. Quantify the number of the one or more labels based on a determination that the series of intensity values consist of the first group of intensity values, the second group of intensity values, the third group of intensity values, and the one or more additional groups of intensity values.

FIGURE 7B

SYSTEMS AND METHODS FOR SINGLE MOLECULE QUANTIFICATION

TECHNICAL FIELD

This application relates generally to computer systems and methods for quantifying labels, and more specifically to computer systems and methods for quantifying single molecules.

BACKGROUND

Recent advancements in detection technologies have enabled detection of single molecules. While the ability to detect single molecules has led to better understanding of properties of individual molecules, it is still challenging to quantify a number of molecules with single-molecule accuracy, especially when the number of molecules is large.

SUMMARY

Accordingly, there is a need for improved devices and methods for quantifying labels with improved sensitivity. In particular, one of the challenges in detecting single molecules arises when multiple labels (or probe products) are located adjacent to one another, which makes it difficult to discern and/or count individual labels (or probe products). The disclosed devices and methods facilitate more accurate quantification of labels (or probe products). Such devices and related methods optionally complement or replace conventional devices and methods for quantifying labels. Such devices and methods provide performance, accuracy, and sensitivity that are not available from conventional devices and methods.

In accordance with some embodiments, a method for quantifying labels on a substrate is performed at an electronic device with one or more processors and memory. The method includes obtaining digital data corresponding to a multi-dimensional (e.g., two-dimensional) measurement over the substrate; and identifying a first set of sub-portions of the digital data. Each sub-portion of the first set of sub-portions is a subset, less than all, of the entire digital data and includes signal of one or more labels. The method also includes, for a respective sub-portion of the first set of sub-portions of the digital data, increasing a quantity of labels; and subtracting a reference signal distribution from the respective sub-portion to obtain subtracted sub-portion data. The method further includes obtaining subtracted digital data. The subtracted digital data includes the subtracted sub-portion data for the respective sub-portion. The method includes identifying a second set of one or more sub-portions of the subtracted digital data. Each sub-portion of the second set of one or more sub-portions is a subset, less than all, of the entire digital data and includes signal of one or more labels. The method includes, for a respective sub-portion of the second set of one or more sub-portions of the subtracted digital data, increasing a quantity of labels.

In accordance with some embodiments, a method for quantifying labels is performed at an electronic device with one or more processors and memory. The method includes obtaining digital data representing a series of intensity values of one or more labels within a particular region over a period of time. The series of intensity values of one or more labels includes intensity values of the one or more labels at respective time frames within the period of time. The series of intensity values of one or more labels includes a first group of intensity values and a second group of intensity values. The method also includes determining from the digital data a first intensity value that represents the first group of intensity values and a second intensity value that represents the second group of intensity values and is distinct from the first intensity value; and quantifying a number of the one or more labels, represented by the digital data, based on at least the first intensity value.

Thus, electronic devices are provided with faster, more efficient methods and interfaces for composing automation rules, thereby increasing the effectiveness, efficiency, and user satisfaction with such devices.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 3B is a block diagram illustrating measurement data in accordance with some embodiments.

FIGS. 6A-6B are flowcharts representing a method of quantifying labels in accordance with some embodiments.

FIGS. 7A-7B are flowcharts representing a method of quantifying labels in accordance with some embodiments.

DETAILED DESCRIPTION

Figure 1:
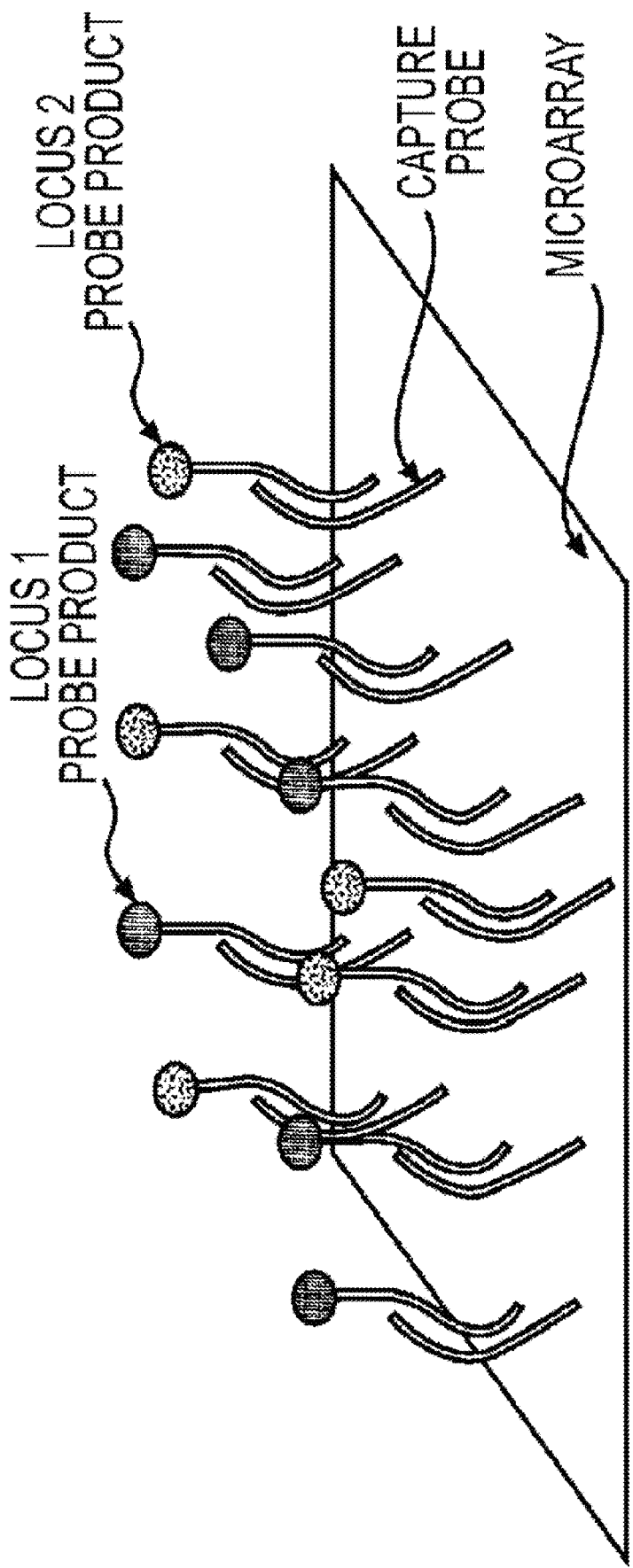
FIG. 1 depicts probe products on a substrate in accordance with some embodiments.

There is a wide range of applications that can benefit from the ability to detect molecules with single-molecule sensitivity or near-single-molecule sensitivity. For example, progress in the human genome project has seeded the need to (i) analyze the expression characteristics of genes and gene products and (ii) analyze the variations in genes and genomes. This has precipitated great interest in methods for large-scale, parallel studies. Interest in developing new methods for detecting variation has further been fuelled by the success of using DNA markers in finding genes for monogenic inherited disorders and recent proposals on large-scale association studies for dissecting complex traits. There is also a need for large-scale studies and high-throughput screening in the search for drugs in the pharmaceutical industry.

This interest in large scale studies may also in the future extend to other areas such as the semiconductor industry where the emergence of devices based on organic molecules such as poly(p-phenylene vinylidene), PPV, and the nascent fields of molecular electronics and nanotechnology seed the demand for new molecules with novel or desirable features and this in turn may seed the need to turn to large scale searching.

In the biotechnology and pharmaceutical sector, large scale studies are preferably done either in homogeneous assays on a microtitre plate (96 well and 384 well plates are common and higher capacity plates are available) or in an array format. Spatially addressable arrays (where the sequence identity of a molecule is specified by the location of the member in which the molecule is contained, within the array of members) of chemical or biochemical species have found wide use in genetics, biology, chemistry and materials science. Arrays can be formed in (i) a disperse solid phase such as beads and bundled hollow fibres/optical fibres, (ii) individual wells of microtitre plates/nanovials, (iii) on a homogeneous medium/surface on which individual members can be spatially addressed or (iv) a surface with nanowells, nanopores or other physical structures. The types of arrays (iii) or (iv) can be made on semi-permeable materials such as gels, gel pads, porous silicon, microchannel arrays (so called 3-D biochips) (Benoit et al; Anal. Chem 2001 73:2412-2420) and impermeable supports such as silicon wafers, glass, gold coated surfaces, ceramics and plastics or any combination of these materials. They can also be made within the walls of microfluidic channels (Gao et al; Nucleic Acids Res. 2001 29: 4744-4750). Furthermore the surface or sub-surface may comprise a functional layer such as an electrode.

In some embodiments, all members in arrays of type (i) and (iii) are contained within a single reaction volume, whilst each member of (ii) is contained in a separate reaction volume.

All members in arrays of the present invention may be contained within a single reaction volume or they may be in a separate reaction volume.

To date, methods have involved analyzing the reactions of molecules in bulk. Although bulk or ensemble approaches have in the past proved useful, there are barriers to progress in a number of directions. The results generated are usually an average of millions of reactions where multiple events, multi-step events and variations from the average cannot be resolved and detection methods that are adapted for high frequency events are insensitive to rare events. The practical limitations associated with bulk analysis include the following:

1. The techniques used for the detection of events in bulk phase analysis are not sensitive enough to detect rare events or small changes/deviations which may be due to low sample amount or weak interaction with probes. a. Detecting the presence of rare transcripts in mRNA profiling. This problem is related to the limited dynamic range of bulk analysis which is in the order of $10^4$ whereas the different abundance levels of mRNAs in a cell are in the $10^5$ range. Hence to cater for the more common events, detection methods are not sensitive enough to detect rare events. b. In the amounts of samples that are usually available to perform genetic analysis there are not enough copies of each sequence in genomic DNA to be detected. Therefore the Polymerase Chain Reaction (PCR) is used to increase the amount of material from genomic DNA so that sufficient signal for detection can be obtained from the desired loci. c. Due to secondary structure around certain target loci very few hybridization events go to completion. The few that do, need to be detected. These events may be too few to be detected by conventional bulk measurements. d. The number of analyte molecules in the sample is vanishingly small. For example, in pre-implantation analysis a single molecule must be analysed. In analysis of ancient DNA the amount of sample material available is often also very small. e. The relative abundance or frequency of two factors of interest (e.g. two different nucleic acid sequences) are very similar and determining their relative frequency with precision and accuracy is challenging with standard methods.

2. A rare event in a background of common events at a particular locus is impossible to detect in the bulk phase due to it being masked by the more common events. There are a number of instances where this is important: a. Detecting loss of heterozygosity (LOH) or copy number change in tumors comprising mixed cell populations and early events in tumorigenesis. b. Determining minimal residual disease in patients with cancer and early detection of relapse by detecting mutation within a wild type background. c. Prenatal diagnosis of genetic disorders directly from the small number of fetal cells in the maternal circulation (hence detection from mother's blood rather than from amniocentesis). d. prenatal diagnostics of genetic disorders from cell-free DNA (cfDNA) where the maternal DNA is usual in far greater abundance than the fetal DNA and so acts to dilute the signal from the fetal DNA. e. Detection of specific alleles in pooled population samples. f. detection of DNA methylation or epigenetic phenomena.

3. It is difficult to resolve heterogeneous events. For example it is difficult to separate out the contribution (or the lack of) to signal from errors such as foldback, mis-priming or self-priming from genuine signals based on the interactions being measured.

4. Complex samples such as genomic DNA, cfDNA and mRNA populations pose difficulties. a. One problem is cross reactions of analyte species within the sample. b. Another problem is the high degree of erroneous interactions which in many cases are likely to be due to mismatch interactions driven by high effective concentrations of certain species. This is one reason for low signal to noise. A ratio as low as 1:1.2 has been used in published array studies for base calling (Cronin et al, Human Mutation 7:244-55, 1996). c. In some cases erroneous interactions can even be responsible for the majority of signal (Mir, K; D. Phil thesis, Oxford University, 1995). d. Detecting a true representative signal of a rare mRNA transcript within a mRNA population is difficult. e. PCR is used in genetic analysis to reduce the complexity of sample from genomic DNA, so that the desired loci become enriched.

5. The bulk nature of conventional methods does not allow access to specific characteristics (particularly, more than one feature) of individual molecules. One example in genetic analysis is the need to obtain genetic phase or haplotype information—the specific alleles associated with each chromosome. Bulk analysis cannot resolve haplotype from a heterozygotic sample. Current molecular biology techniques that are available, such as allele-specific or single molecule PCR are difficult to optimize and apply on a large scale.

6. Transient processes are difficult to resolve. This is needed when deciphering the molecular mechanisms of processes. Also transient molecular binding events (such as nucleation of a hybridization event which is blocked from propagation due to secondary structure in the target) have fractional occupancy times which cannot be detected by conventional solid-phase binding assays.

When two samples are compared, small differences in concentration (less than twofold difference) are difficult to unequivocally discern.

Microarray gene expression analysis using unamplified cDNA target typically requires $10^6$ cells or 100 micrograms of tissue. Neither expression analysis nor analysis of genetic variation can be performed directly on material obtained from a single cell which would be advantageous in a number of cases (e.g. analysis of mRNA from cells in early development or genomic DNA from sperm).

Further, it would be highly desirable if the amplification processes that are performed before most biological or genetic analysis could be avoided (e.g. amplification of the sample prior to analysis).

PCR is used for the analysis of Variable Number of Tandem Repeats is central to Forensics and Paternity testing. Linkage studies have traditionally used Short Tandem repeats as markers analysis which is performed by PCR.

The need to avoid PCR is particularly acute in the large scale analysis of SNPs. The need to design primers and perform PCR on a large number of SNP sites presents a major drawback. The largest scales of analysis that are currently being implemented (e.g. using Orchid Bioscience and Sequenom systems) remain too expensive to allow meaningful association studies to be performed by all but a few large organizations such as the Pharmaceutical companies. Although, the number of SNPs needed for association studies has been actively debated, the highest estimates are being revised down due to recent reports that there are large blocks of linkage disequilibrium within the genome. Hence, the number of SNPS needed to represent the diversity in the genome could be 10 fold fewer than was expected. However, this needs to be taken with the caveat that there are some regions of the genome where the extent of linkage disequilibrium is far lower and a greater number of SNPs would be needed to represent the diversity in these areas. Even so, if each site had to be amplified individually the task would be enormous. In practice, PCR can be multiplexed. However, the extent to which this can be done is limited and increased errors, such as primer-dimer formation and mismatches as well as the increased viscosity of reaction, present barriers to success and limits multiplexing to around ten sites in most laboratories.

It is clear that the cost of performing SNP detection reactions on the scale required for high-throughput analysis of polymorphisms in a population is prohibitive if each reaction needs to be conducted separately, or if only a limited multiplexing possibility exists. A highly multiplexed, simple and cost-effective route to SNP analysis will be required if the potential of pharmacogenomics, pharmacogenetics as well as large-scale genetics is to be realized. DNA pooling is a solution for some aspects of genetic analysis but accurate allele frequencies must be obtained which is difficult especially for rare alleles.

Since it involves determining the association of a series of alleles along a single chromosome, the haplotype is thought to be far more informative than the analysis of individual SNP. An international effort is underway for making a comprehensive haplotype map of the human genome. Generally, haplotypes are determined by long-range allele specific PCR. However, the construction of somatic cell hybrids prior to haplotype determination is an alternative method.

A method for haplotyping on single molecules in solution has been proposed in patent (WO 01/90418). However, in this method the molecules are not surface captured, positional information of the SNP is not obtained and each SNP must be coded with a different color.

For several years, plans for large scale SNP analysis have been laid around the common disease-common variant (CD/CV) (i.e. common SNP) hypothesis of complex diseases (Reich D E and Lander E S Trends Genet 17: 502-50 2001). The SNP consortium has amassed more than a million putatively common SNPs. However practical use of this set is confounded by the fact that different SNPs may be common in different ethnic populations and many of the putative SNPs may not be truly polymorphic. Furthermore, the CD/CV hypothesis has recently come under challenge from assertions that rare alleles may contribute to the common diseases (Weiss K M, Clark A G, Trends Genet 2002 January; 18(1):19-24). If this were the case, although "new" rare alleles would be sufficiently in linkage disequilibrium with a common SNP for the association with the region that contains both to be successfully made, if the allele was "ancient" and rare then the common SNPs and haplotype maps would not represent the diversity. In this scenario alternative strategies are needed to find causative regions. Instead of genome-wide scan of common SNPs it may be that there will be a need for whole genome sequencing or re-sequencing of thousands of case and control samples to access all variants. The commercial sequencing of the human genome, which built on information from the public genome project, cost approximately 300 million dollars over a period of about one year. This cost and timescale is prohibitive as an alternative to SNP analysis for finding associations between DNA sequence and disease. Clearly, if sequencing is to replace current approaches to large scale genetic studies, radically different methods are needed.

It would be advantageous if sequencing runs could be on the scale of genomes or at least small genomes or whole genes. Even increasing read-lengths beyond 300-500 nt would be useful. A number of sequencing methods are available including: 1 Sequencing by synthesis; 2 Direct analysis of the sequence of a single molecule; 3 Sequencing by Hybridization; and 4 Sanger Sequencing.

Re-sequencing by chip methods is an alternative to de-novo sequencing. The 21.7 million bases of non-repetitive sequence of chromosome 21 has recently been re-sequenced by chip methods by Patil et al (Science 294: 1719-1722, 2001). The haplotype structure was conserved in this study by making somatic cell hybrids prior to chip analysis. However, the cost of large scale re-sequencing by this method is still high and only 65% of the bases that were probed gave results of enough confidence for the base to be called.

The disclosed devices and methods reduce or eliminate such problems by facilitating more accurate quantification of labels (or probe products). Such devices and related methods optionally complement or replace conventional devices and methods for quantifying labels. Such devices and methods provide performance, accuracy, and sensitivity that are not available from conventional devices and methods.

FIG. 1 depicts probe products on a substrate in accordance with some embodiments. In FIG. 1, probe products of different types (e.g., a locus 1 probe product and a locus 2 probe product) are used. In one example, the locus 1 probe product is configured for one genomic locus and the locus 2 probe product is configured for another genomic locus. The locus 1 probe product is coupled with a first label (e.g., a fluorophore with a first color, such as red), and the locus 2 probe product is coupled with a second label (e.g., a fluorophore with a second color that is distinct from the first color, such as green). In some embodiments, a single probe product (e.g., the locus 1 probe product or the locus probe product) is labeled with multiple labels (e.g., a group of multiple fluorophores). The probe products are described in detail in U.S. Pat. No. 9,212,394 and International Application No. PCT/US2016/018549, which are incorporated by reference herein in their entireties.

In some embodiments, the probe products are immobilized on a substrate (e.g., by hybridization to capture probes on a microarray), as shown in FIG. 1. Scanning the substrate (e.g., collecting an image of the substrate) provides digital data, from which individual labels can be detected and quantified.

Figure 2:
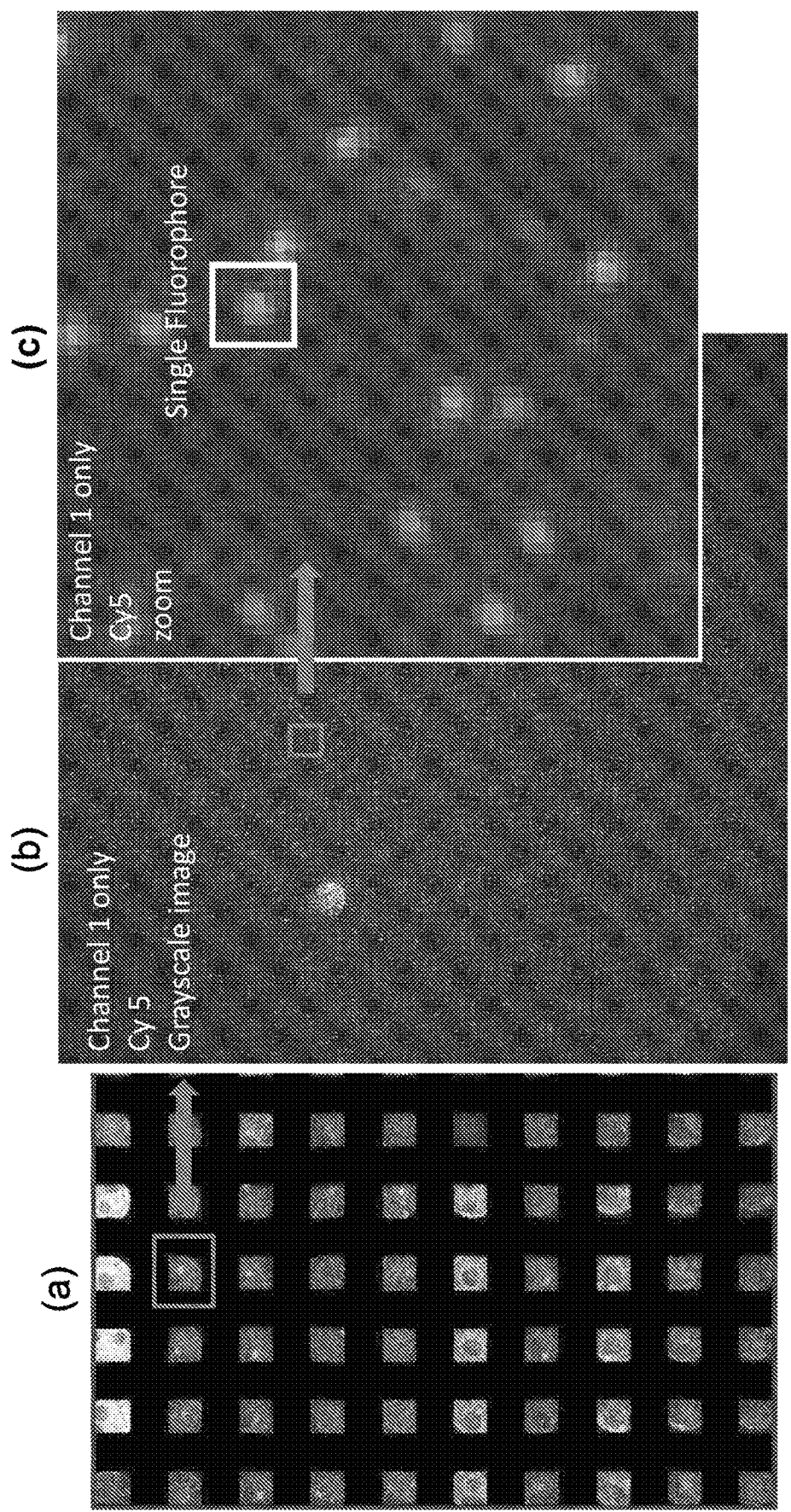
FIG. 2 depicts exemplary digital data (e.g., digital images) in accordance with some embodiments.

FIG. 2 depicts exemplary digital data (e.g., digital images) in accordance with some embodiments.

The image (a) in FIG. 2 is an example of digital data (e.g., multi-dimensional digital image, such as two-dimensional digital image) collected from a substrate. The image (a) shows that labels are arranged in a grid pattern (e.g., by printing or spotting in a grid pattern capture probes, which, in turn, captures the labels or probe products in the grid pattern). In the image (a) of FIG. 2, each spot has a rectangular or square shape. Each spot shown in the image (a) contains a large number of labels (or probe products). In some embodiments, images of spots are collected at a higher magnification. In some embodiments, one or more areas between two adjacent spots (shown in black) are not imaged.

The image (b) in FIG. 2 is an enlarged view of a spot in the image (a). In the image (b), a number of labels (or probe products) are shown.

The image (c) in FIG. 2 is an enlarged view of a portion of a spot in the image (b). In the image (c), individual labels (e.g., single fluorophore) can be detected.

However, in some cases, it is difficult to determine what appears to be a single label contains only one label, especially when two labels are located adjacent to each other (e.g., a distance between the two labels is less than a diffraction limit of an optical imaging system).

Figure 3A:
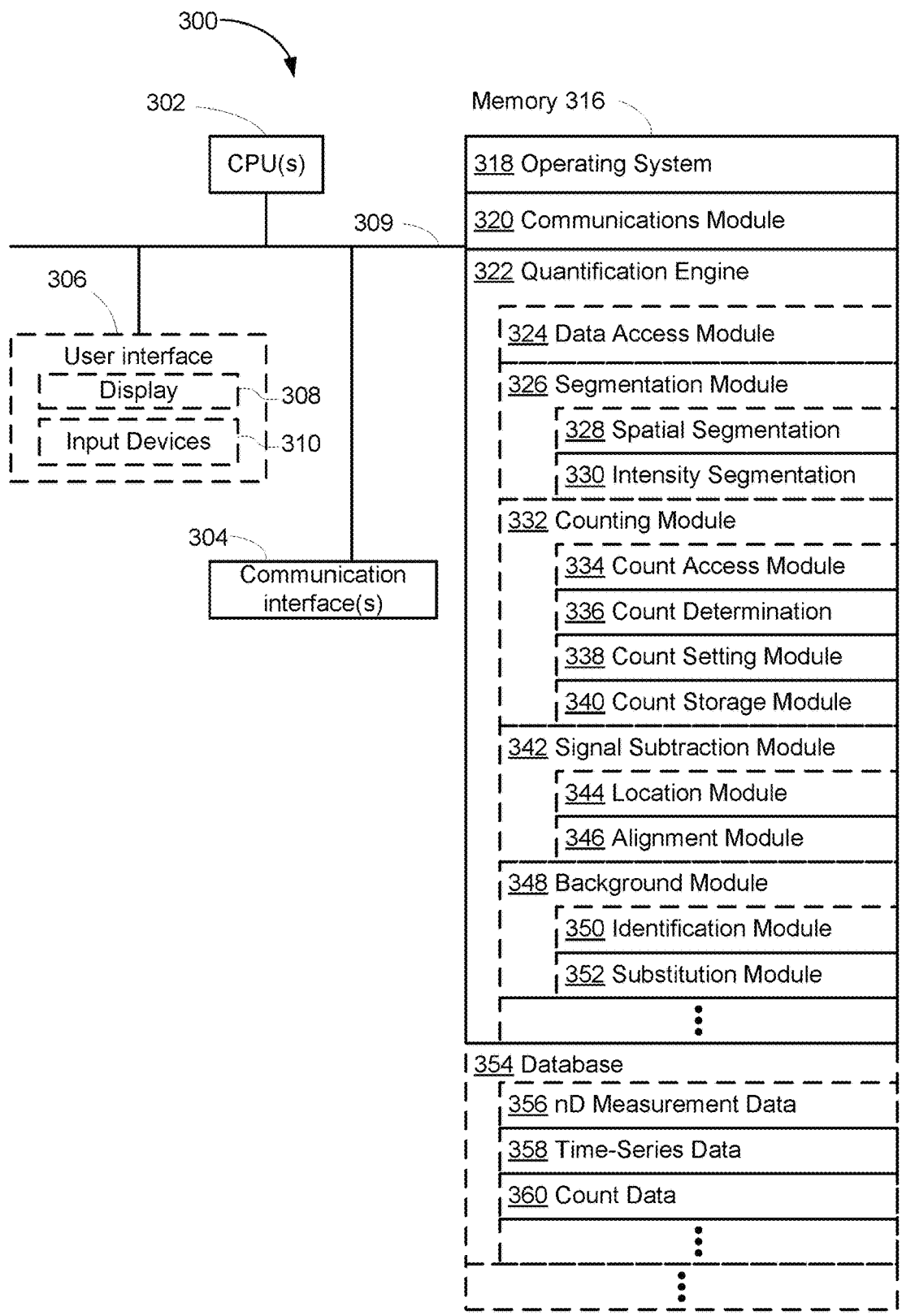
FIG. 3A is a block diagram illustrating an electronic device in accordance with some embodiments.

FIG. 3A is a block diagram illustrating electronic device 300 in accordance with some embodiments. Device 300 is configured for quantifying labels, which reduces or eliminates the challenges that arise when multiple labels are located adjacent to one another.

Device 300 typically includes one or more processors 302 (e.g., microprocessors, central processing units (CPUs), accelerated processing units (APU), etc.), one or more network or other communications interfaces 304, memory 316, and one or more communication buses 308 for interconnecting these components. In some embodiments, one or more processors 302 and memory 316 are integrated (e.g., application-specific integrated circuit or field-programmable gate array). In some embodiments, communication buses 309 include circuitry (sometimes called a chipset) that interconnects and controls communications between system components. In some other embodiments, device 300 includes user interface 306 (e.g., a user interface having display device 308 and input devices 310, such as a keyboard, a mouse, a touchpad, a touch screen, and/or other pointing device).

Communication interfaces 304 include one or more circuits for wired and/or wireless communications. In some embodiments, communication interfaces 304 include radio frequency (RF) circuit. The RF circuit receives and sends RF signals, also called electromagnetic signals. The RF circuit converts electrical signals to/from electromagnetic signals and communicates with communications networks and other communications devices via the electromagnetic signals. The RF circuit optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuit optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Memory 316 of device 300 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 316 may optionally include one or more storage devices remotely located from processor(s) 302. Memory 316, or alternately the non-volatile memory device(s) within memory 316, comprises a computer readable storage medium. In some embodiments, memory 316, or the non-volatile memory device(s) within memory 316, comprises a non-transitory computer readable storage medium. In some embodiments, memory 316 or the computer readable storage medium of memory 316 stores the following programs, modules and data structures, or a subset thereof:

Operating System 318 that includes procedures for handling various basic system services and for performing hardware dependent tasks;

Network Communication Module (or instructions) 320 that is used for connecting device 300 to other computers (e.g., clients) or devices (e.g., mobile phones, tablets, etc.) via one or more network interfaces 304 and one or more communications networks, such as the Internet, other wide area networks, local area networks, metropolitan area networks, and so on;

Quantification Engine 322 for quantifying labels based on digital data; and

Database 354 for storing data used in quantifying labels.

In some embodiments, quantification engine 322 includes the following programs, modules and data structures, or a subset or superset thereof:

Data Access Module 324 for assisting access to database 354, such as locating, retrieving, and storing data in database 354 (e.g., data access module 324 includes an application programming interface for accessing data stored in database 354);

Segmentation Module 326 for segmenting data (e.g., intensity values) based on spatial information, intensity information, and/or time-domain information;

Counting Module 332 for counting, quantifying, and/or quantitating labels;

Signal Subtraction Module 342 for subtracting label signals from digital data; and Background Module 348 for subtracting background signals from digital data.

In some embodiments, segmentation module 326 includes one or more of: spatial segmentation module 328 for segmenting multi-dimensional measurement data (e.g., segmenting a two-dimensional image into multiple regions) and/or intensity segmentation module 330 for segmenting data based on intensity values (e.g., segmenting time-series data based on intensity values).

In some embodiments, counting module 332 includes one or more of: count access module 334 for retrieving count data 360 from database 354; count determination module 336 for determining quantities of labels (e.g., by counting or based on grouping of intensity values); count setting module 338 (e.g., adjusting determined counts); and/or count storage module 340 (e.g., storing count data 360 in database 354).

In some embodiments, signal subtraction module 342 includes one or more of: location module 344 for identifying a peak location in multi-dimensional measurement data (e.g., identifying a location of a label in a two-dimensional image of a substrate) and/or alignment module 346 for aligning a reference signal (e.g., aligning a point-spread-function of a single label to the identified location of the label).

In some embodiments, background module 348 includes one or more of: identification module 350 for identifying a background intensity and/or substitution module 352 for replacing background intensity in time-series data 358 with an intensity of a label.

In some embodiments, database 354 includes the following data structures, or a subset or superset thereof:

Multi-dimensional Measurement Data 356 (e.g., two-dimensional images of labels on substrates), which is described below with respect to FIG. 3B;

Time-Series Data 358 (e.g., intensity values over a period of time), which is described below with respect to FIG. 3C; and Counts Data 360 (e.g., the number of labels at respective locations), which is described below with respect to FIG. 3D.

Each of the above identified software systems, procedures, modules, and applications correspond to a set of instructions for performing one or more functions described above. These modules (i.e., sets of instructions) need not be implemented as separate software programs, procedures, or modules, and thus various subsets of these modules may be combined or otherwise re-arranged in various embodiments. In some embodiments, memory 316 may store a subset of the modules and data structures identified above. Furthermore, memory 316 may store additional modules and data structures not described above.

The actual number of servers used to implement device 300 and how features are allocated among them will vary from one implementation to another, and may depend in part on the amount of data traffic that the system must handle during peak usage periods as well as during average usage periods, and may also depend on the amount of data stored by the distributed computing system. Moreover, one or more of the blocks in FIG. 3A may be implemented on one or more servers designed to provide the described functionality (e.g., segmentation module 326 and background module 348 may be implemented on two separate servers).

FIG. 3B is a block diagram illustrating multi-dimensional measurement data 356 in accordance with some embodiments.

In some embodiments, multi-dimensional measurement data 356 includes multiple sets of multi-dimensional measurement data as shown in FIG. 3B (e.g., multiple two-dimensional images). In some embodiments, a respective set of multi-dimensional measurement data includes a two-dimensional array of intensity values 370 (e.g., 370-1 through 370-N+8), where each intensity value 370 corresponds to a particular location. For example, when the respective set of multi-dimensional measurement data includes a two-dimensional image of a substrate (or labels located on the substrate), each pixel in the image contains an intensity value for a corresponding location on the substrate.

Figure 3C:
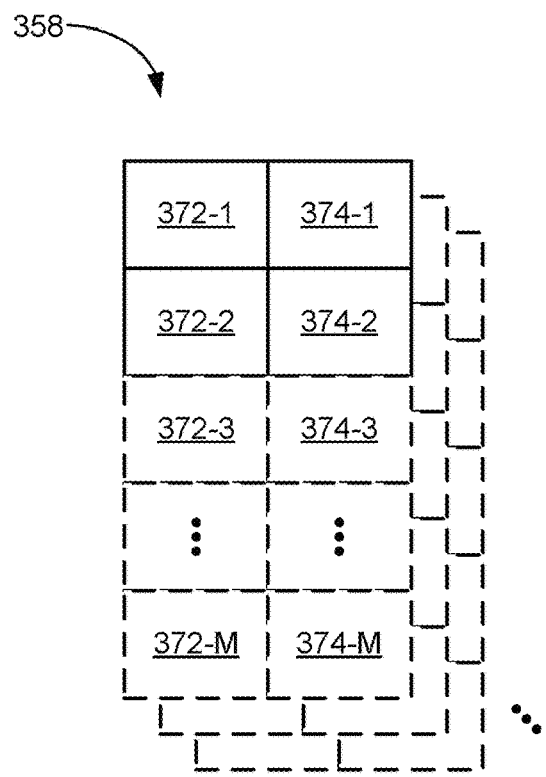
FIG. 3C is a block diagram illustrating time-series data in accordance with some embodiments.

FIG. 3C is a block diagram illustrating time-series data 358 in accordance with some embodiments.

In some embodiments, time-series data 358 includes multiple sets of time-series data, as shown in FIG. 3C. In some embodiments, a respective set of time-series data includes time stamp 372 (e.g., 372-1 through 372-M) and corresponding intensity value 374 (e.g., 374-1 through 374-M).

Figure 3D:
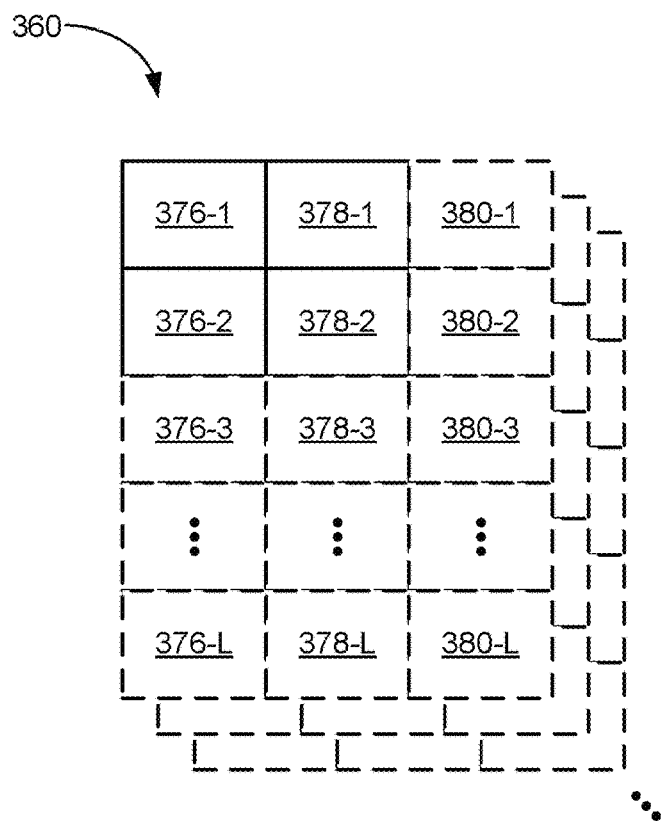
FIG. 3D is a block diagram illustrating count data in accordance with some embodiments.

FIG. 3D is a block diagram illustrating count data 360 in accordance with some embodiments.

In some embodiments, count data 360 includes multiple sets of count data, as shown in FIG. 3D. In some embodiments, a respective set of count data includes location indicators 376 and 378 (e.g., x-coordinate and y-coordinate of a sub-region of the multi-dimensional measurement data) and corresponding intensity value 380.

Figure 4A:
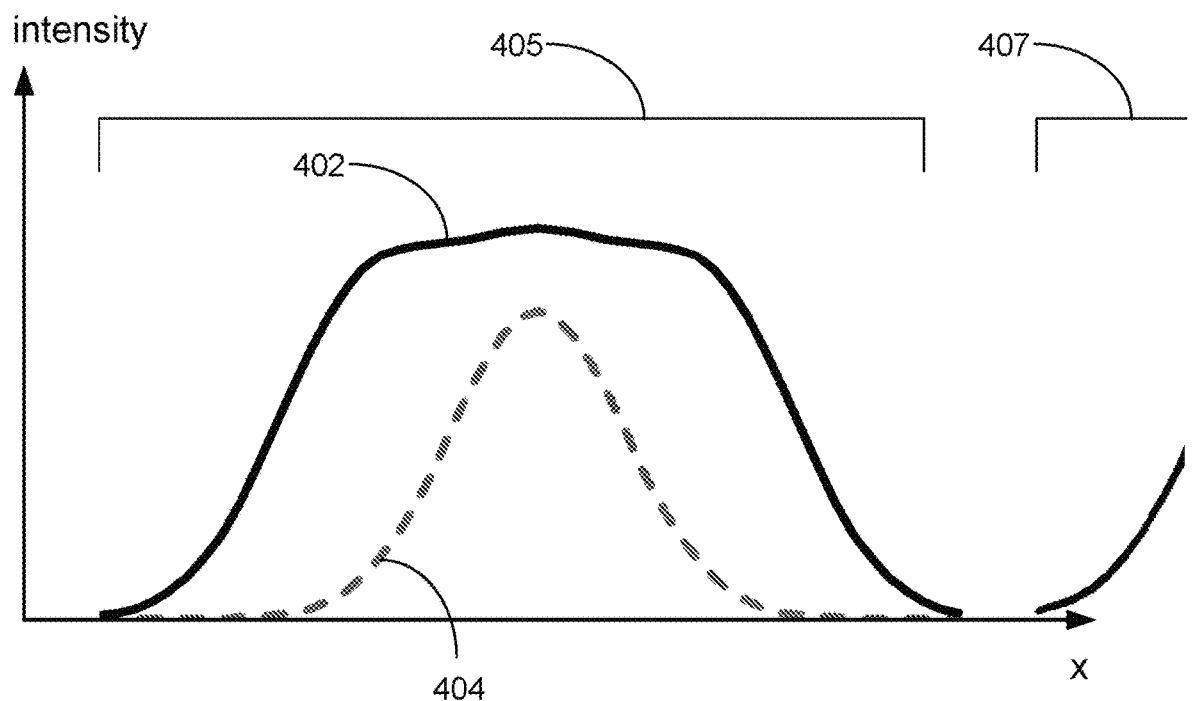
FIGS. 4A-4C illustrate a prophetic example of quantifying labels in accordance with some embodiments.
Figure 4B:
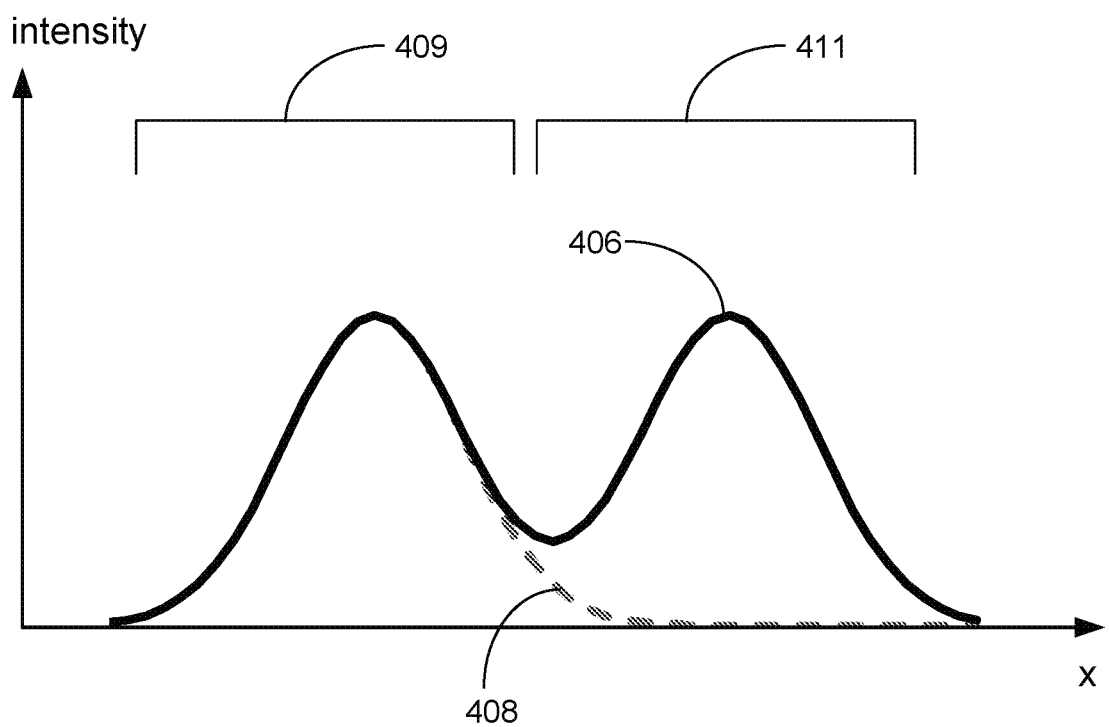
Figure 4C:
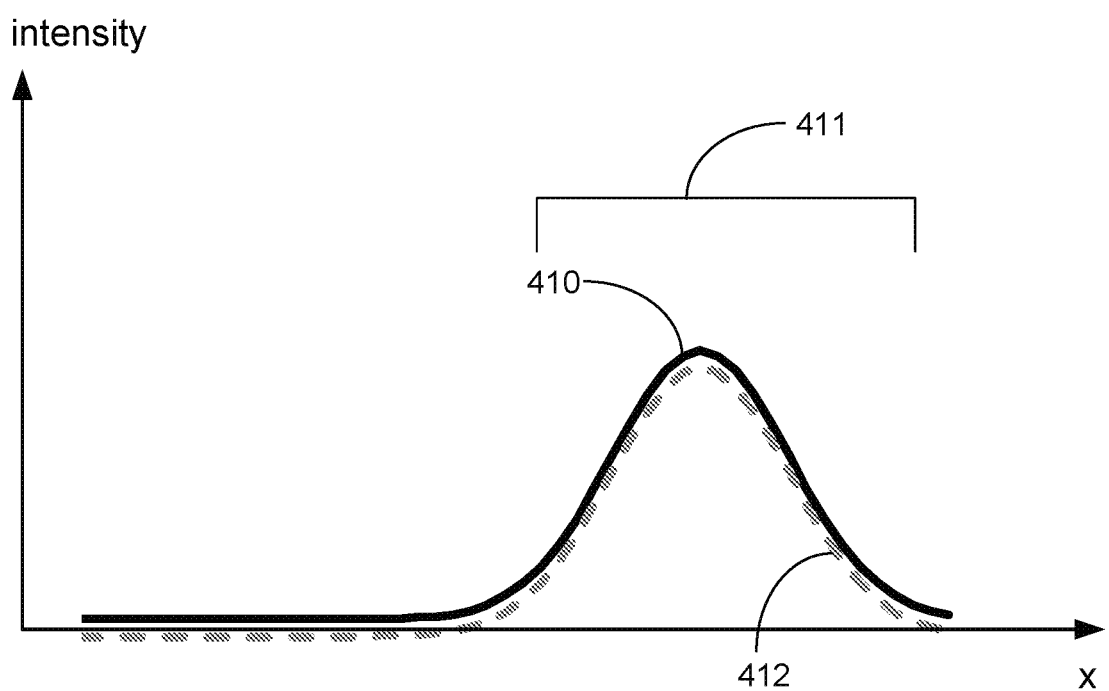

FIGS. 4A-4C illustrate a prophetic example of quantifying labels in accordance with some embodiments.

FIG. 4A shows exemplary intensity profile 402. Measured data are typically multi-dimensional (e.g., measured data includes a two-dimensional image or three-dimensional data). However, for simplicity, subtraction operations are described herein with respect to one-dimensional data illustrated in FIGS. 4A-4C. A person having ordinary skill in the art would understand that subtraction operations can be applied to multi-dimensional data in an analogous manner.

The intensity profile shown in FIG. 4A includes two regions 405 and 407. In some embodiments, the two regions are identified using a watershed method (e.g., a gradient of intensity values is determined and a watershed method is applied on the gradient or an absolute value of the gradient). In some embodiments, the two regions 405 and 407 are identified using the Minimum Spanning Forest method. Such segmentation of the digital data facilitates detection and/or quantification of labels, because regions that do not contain signals of labels are not analyzed further, thereby reducing the computational load. For example, a region between region 405 and region 407 is not processed further. In some embodiments, regions that contain signals of intensity above a predefined threshold are identified as regions that contain signals of labels.

FIG. 4A also shows that a peak location of a signal from a label is identified. In some embodiments, a centroid of region 405 is identified as the peak location. In some embodiments, a maximum intensity value of intensity profile 402 within region 405 is identified as the peak location. In some embodiments, intensity profile 402 is fit with a profile of a reference signal in order to determine the peak location.

In some embodiments, in accordance with a determination that intensity profile 402 within region 405 is equal to, or greater than, reference signal 404 of a label at the identified peak location, it is determined that at least one label is present within region 405.

In some embodiments, reference signal 404 of a label at the identified peak location is subtracted from intensity profile 402 to obtain adjusted intensity profile 406 (shown in FIG. 4B).

FIG. 4B illustrates adjusted intensity profile 406, which corresponds to intensity profile 402 less reference signal 404 (e.g., a difference between intensity profile 402 and reference signal 404 at the identified peak location).

In some embodiments, region 405 is further segmented into regions 409 and 411 (e.g., using the watershed method or any other suitable methods). In some embodiments, further analysis (e.g., identification of a peak location, subtraction of a reference signal, etc.) is performed for region 409 and/or region 411 instead of entire region 405. In some other embodiments, further analysis is performed for the entire region 405, thereby eliminating the need for further segmentation of region 405.

FIG. 4B also shows that a second peak location of a signal from a label within region 409 is identified. In some embodiments, in accordance with a determination that adjusted intensity profile 406 is equal to, or greater than, reference signal 408 of a label at the second identified peak location, it is determined that at least one label is present within region 409.

In some embodiments, reference signal 408 of a label at the second identified peak location is subtracted from adjusted intensity profile 406 to obtain second adjusted intensity profile 410 (shown in FIG. 4C).

FIG. 4C illustrates second adjusted intensity profile 410, which corresponds to intensity profile 406 less reference signal 408 (e.g., a difference between intensity profile 406 and reference signal 408 at the second identified peak location).

In some embodiments, further segmentation is performed on second adjusted intensity profile 410. In some other embodiments, segment 405 or segment 411 is used for further analysis of second adjusted intensity profile 410.

FIG. 4C also shows that a third peak location of a signal from a label within region 411 is identified. In some embodiments, in accordance with a determination that adjusted intensity profile 410 is equal to, greater than, reference signal 412 of a label at the third identified peak location, it is determined that at least one label is present within region 411.

In some embodiments, reference signal 412 is a label at the third identified peak location is subtracted from second adjusted intensity profile 410 to obtain a third adjusted intensity profile.

In some embodiments, the segmentation, peak location determination, and/or reference signal subtraction operations described above are repeated. In some embodiments, the segmentation, peak location determination, and/or reference signal subtraction operations described above are repeated until an intensity of an adjusted intensity profile is less than a predefined threshold (e.g., an average, median, or maximum intensity value of the adjusted intensity profile is less than the predefined threshold).

Thus, based on the operations described above with respect to FIGS. 4A-4C, it has been determined that intensity profile 402 contains signals of three labels (e.g., a first label at the identified peak location, a second label at the second identified peak location, and a third label at the third identified peak location).

Analogous operations can be performed with respect to other regions (e.g., region 407 shown in FIG. 4A). In some embodiments, such operations are performed concurrently (e.g., analysis of region 405 is performed concurrently with analysis of region 407).

Figure 5A:
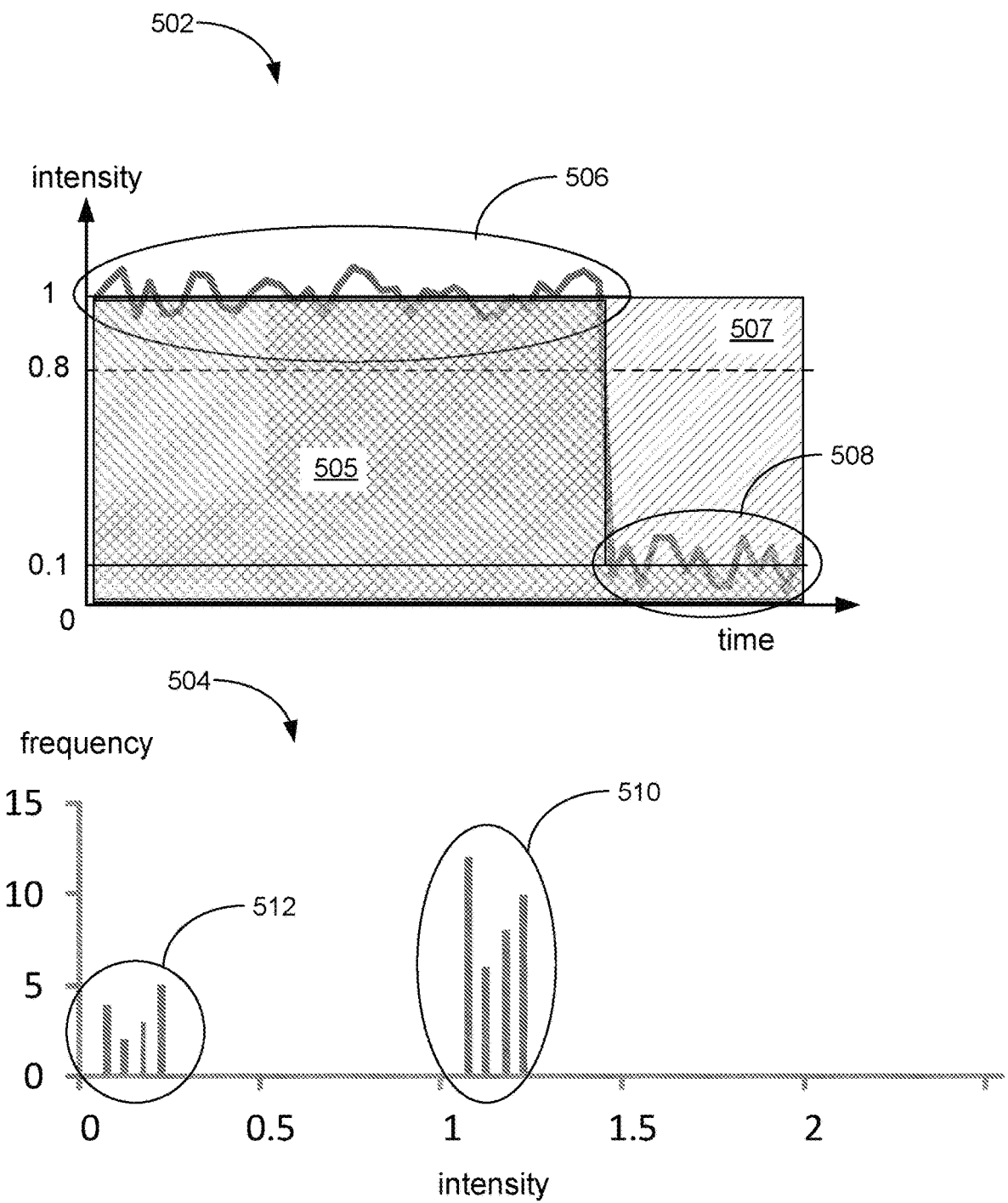
FIGS. 5A-5B illustrate a prophetic example of quantifying labels in accordance with some embodiments.
Figure 5B:
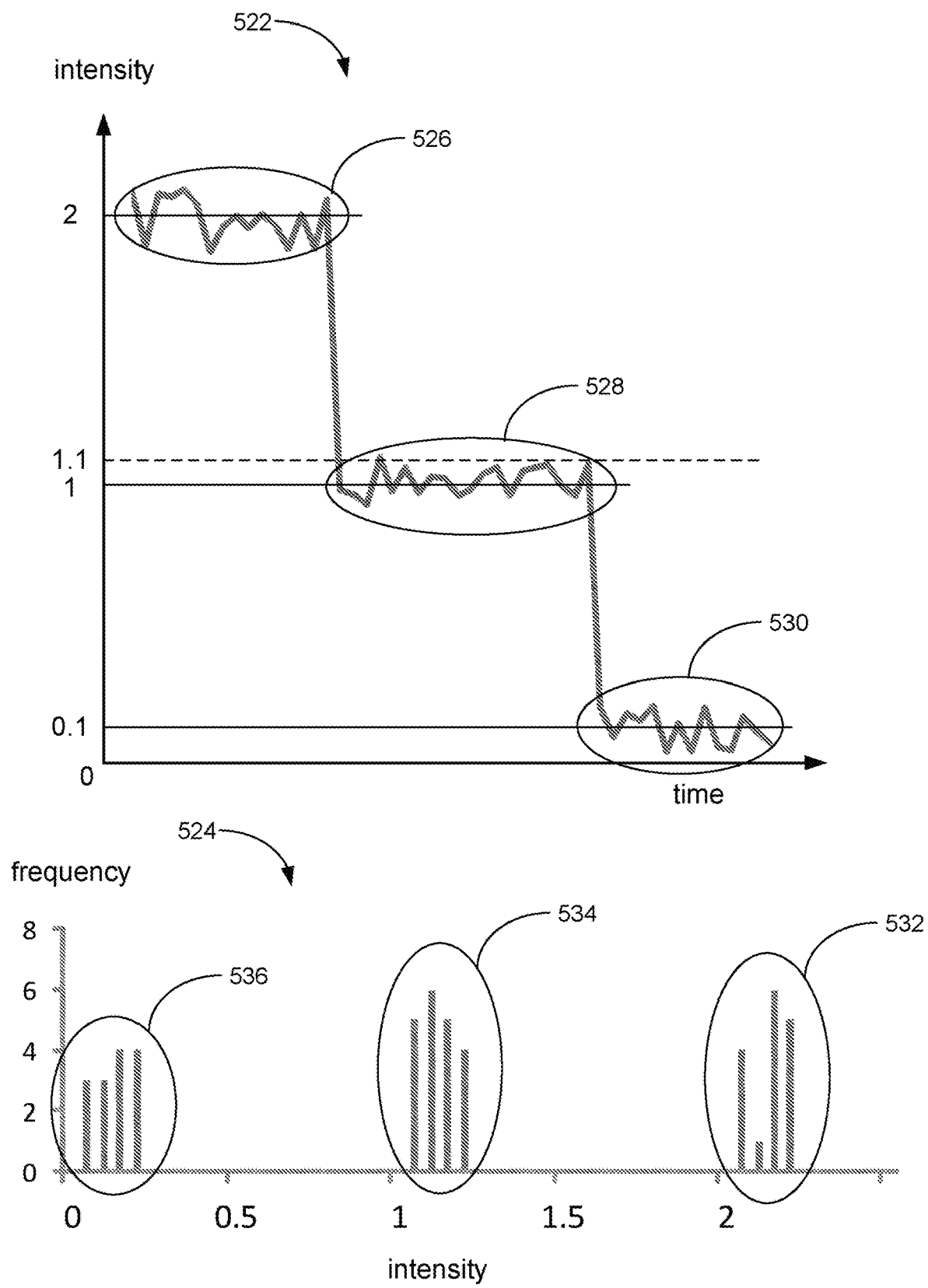

FIGS. 5A-5B illustrate prophetic examples of quantifying labels in accordance with some embodiments.

FIG. 5A shows intensity plot 502 of intensity values measured from a label (or a particular location) over a period of time and histogram 504 of the intensity values. Intensity values in intensity plot 502 are initially clustered around a first intensity value (e.g., 1). After a period of time, the intensity is reduced to intensity values around a second intensity value (e.g., 0.1) that is distinct from the first intensity value. For example, photobleaching of a fluorophore causes such a decrease in intensity over time.

If the signal of the label is measured in a single measurement over a particular period of time (e.g., 10 seconds), the measured intensity would correspond to an average intensity of 0.8 for the particular period of time, thereby increasing an error in quantifying labels. Sequentially measuring the intensity in multiple frames over a same period of time allows detection of intensity values before the reduction (e.g., due to photobleaching), and appropriate corrections can be made to compensate for the reduction. For example, instead of simply adding, or calculating an average of, all of the intensity values measured over the particular period time (e.g., area 505 determined by adding all of the intensity values measured over the particular period of time), reduced intensity values 508 are replaced with a representative value (e.g., an average, median, weighted average etc.) of non-reduced intensity values 506. In turn, a sum or an average of non-reduced intensity values 506 and the substituting value (e.g., the representative value of non-reduced intensity values 506) is determined and used for quantifying labels (e.g., area 507 determined using non-reduced intensity values 506 and the substituting value). Alternatively, a sum or an average of intensity values other than non-reduced intensity values 506 is determined, and the sum or the average is adjusted by a fraction of time (or a fraction of frames) in which non-reduced intensity values 506 have been measured. For example, when non-reduced intensity values 506 have been measured in seven out of ten frames, the sum or the average is adjusted by a factor of 0.7 (e.g., by dividing with 0.7).

In some embodiments, non-reduced intensity values 506 and reduced intensity values 508 are identified from the measured intensity values. In some embodiments, non-reduced intensity values 506 and reduced intensity values 508 are identified based on statistics of such intensity values. For example, histogram 504 shows that bins 510 that correspond to non-reduced intensity values 506 have a first distribution in histogram 504 (e.g., bins 510 are clustered around the first intensity value, such as 1), and bins 512 that correspond to reduced intensity values 508 have a second distribution in histogram 504 (e.g., bins 512 are clustered around the second intensity value, such as 0.1). In some embodiments, a standard deviation of the distribution of the intensity values is used to distinguish bins 510 (corresponding to non-reduced intensity values 506) and bins 512 (corresponding to reduced intensity values 508). For example, reduced intensity values 508 are more than three times standard deviation of non-reduced intensity values 506 away from an average of non-reduced intensity values 506, and/or non-reduced intensity values 506 are more than three times standard deviation of reduced intensity values 508 away from an average of reduced intensity values 508.

In some embodiments, the number of labels is determined to be one based on grouping of the intensity values into two groups: a first group of bins 510 and a second group of bins 512.

FIG. 5B shows intensity plot 522 of intensity values measured from labels (or a particular location) over a period of time and histogram 524 of the intensity values. Intensity values in intensity plot 522 are initially clustered around a first intensity value (e.g., 2). After a period of time, the intensity is reduced to intensity values around a second intensity value (e.g., 1) that is distinct from the first intensity value. Thereafter, the intensity is further reduced to intensity values around a third intensity value (e.g., 0.1) that is distinct from the first intensity value and the second intensity value. As explained above, photobleaching of a fluorophore causes such decreases in intensity over time.

If the signal of the label is measured in a single measurement over a particular period of time (e.g., 10 seconds), the measured intensity would correspond to an average intensity of 1.1 for the particular period of time, thereby increasing an error in quantifying labels (e.g., although there are two labels, the average intensity is close to an intensity of a single label). Sequentially measuring the intensity in multiple frames over a same period of time allows detection of intensity values before the reduction (e.g., due to photobleaching), and appropriate corrections can be made to compensate for the reduction. For example, instead of simply adding, or calculating an average of, all of the intensity values measured over the particular period time, reduced intensity values 528 and 530 are replaced with a representative value (e.g., an average, median, etc.) of non-reduced intensity values 526. In turn, a sum or an average of non-reduced intensity values 526 and the substituting value (e.g., the representative value of non-reduced intensity values 526) is determined and used for quantifying labels.

In some embodiments, non-reduced intensity values 526 and reduced intensity values 528 and 530 are identified from the measured intensity values. In some embodiments, non-reduced intensity values 526 and reduced intensity values 528 and 530 are identified based on statistics of such intensity values. For example, histogram 524 shows that bins 532 that correspond to non-reduced intensity values 526 have a first distribution in histogram 504 (e.g., bins 532 are clustered around the first intensity value, such as 2), bins 534 that correspond to reduced intensity values 528 have a second distribution in histogram 524 (e.g., bins 534 are clustered around the second intensity value, such as 1), and bins 536 that correspond to reduced intensity values 530 have a third distribution in histogram 524 (e.g., bins 536 are clustered around the third intensity value, such as 0.1). In some embodiments, a standard deviation of the distribution of the intensity values is used to distinguish bins 532 (corresponding to non-reduced intensity values 526), bins 534 (corresponding to reduced intensity values 528), and bins 536 (corresponding to reduced intensity values 530). For example, reduced intensity values 528 are more than three times standard deviation of non-reduced intensity values 526 away from an average of non-reduced intensity values 526, reduced intensity values 528 are more than three times standard deviation of reduced intensity values 530 away from an average of reduced intensity values 530, non-reduced intensity values 526 are more than three times standard deviation of reduced intensity values 528 away from an average of reduced intensity values 528, and/or reduced intensity values 530 are more than three times standard deviation of reduced intensity values 528 away from an average of reduced intensity values 528.

In some embodiments, the number of labels is determined to be two based on grouping of the intensity values into three groups: a first group of bins 532, a second group of bins 534, and a third group of bins 536.

In some embodiments, the number of labels is determined based on the number of groups into which the intensity values are grouped (e.g., if the intensity values are divided into four groups, three labels are present, and if the intensity values are divided into N groups, (N−1) labels are present).

Although intensity reduction illustrated in FIGS. 5A-5B is described above in connection with photobleaching, the intensity may vary for other reasons. For example, certain single molecules (e.g., fluorophores) are known to blink (e.g., changes its intensity over time, as if the molecule turns on and off). The effect of such changes can be also reduced or eliminated by using the method described above with respect to FIGS. 5A and 5B. For brevity, such details are not repeated herein.

Figure 5C:
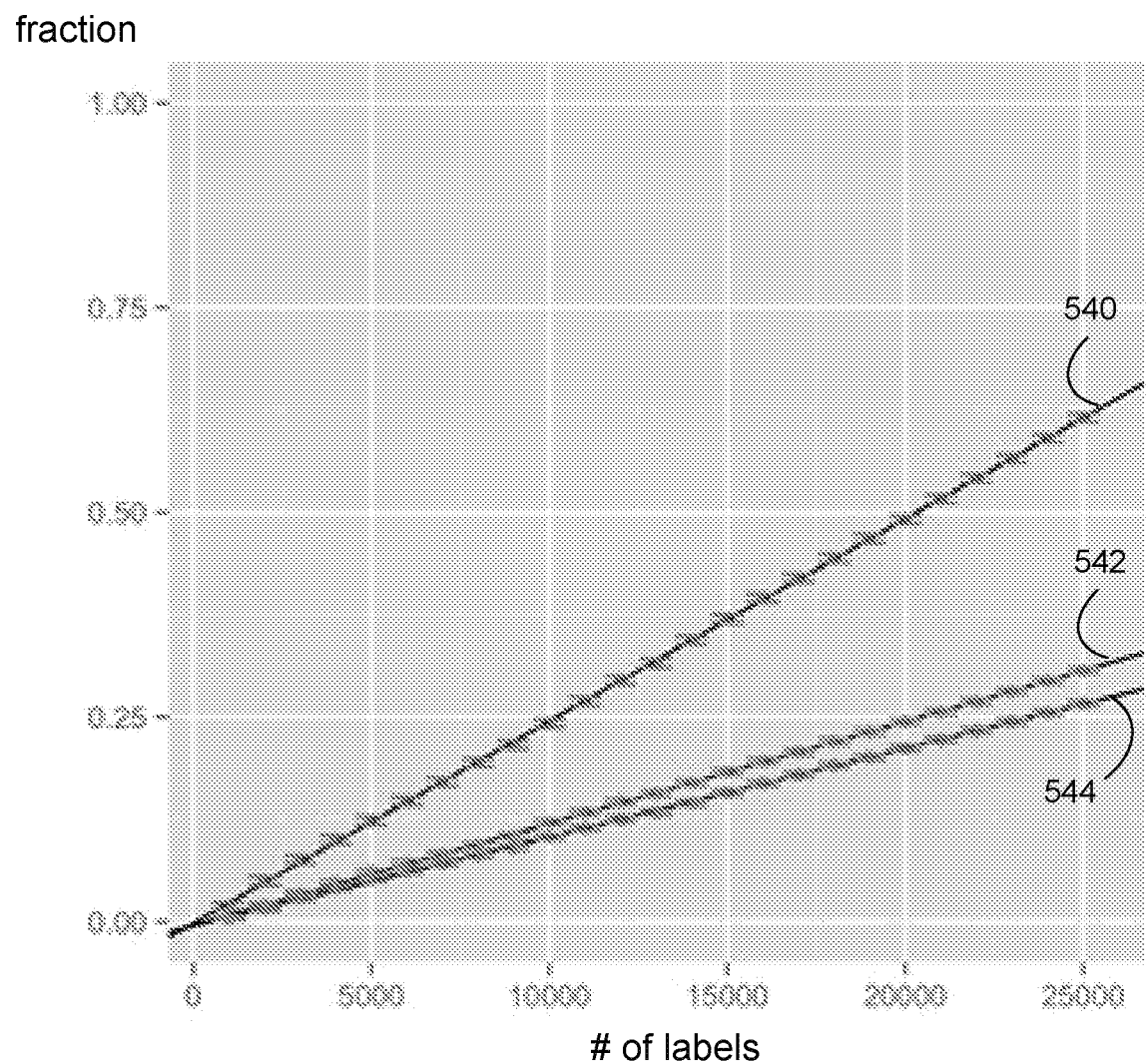
FIG. 5C illustrates a prosphetic example of verifying a count of labels in accordance with some embodiments.

FIG. 5C illustrates a prophetic example of verifying a count of labels in accordance with some embodiments.

When a few labels are placed on a large surface at random, the labels are likely to spread out (e.g., no overlapping labels) so that the labels can be easily counted. When a density of the labels increases, one or more labels will be placed adjacent to other labels so that it would be difficult to count them separately without the methods described above with respect to FIGS. 4A-4C and 5A-5B. A fraction of "overlapping" labels (e.g., labels that are located adjacent to other labels within a resolution of an imaging system) over a total number of labels is a function of a number of imaged labels. As shown in FIG. 5C, the fraction of overlapping labels increases linearly with the concentration of labels (e.g., line 542). FIG. 5C also shows that the fraction of overlapping labels is affected by a resolving power of an optical system that was used to collect the images. For example, when the resolving power of the optical system increases (e.g., a lower Rayleigh limit), the fraction of overlapping labels decreases (e.g., line 544). When the resolving power of the optical system decreases (e.g., a higher Rayleigh limit), the fraction of overlapping labels increases (e.g., line 540).

This relationship between the fraction of overlapping labels and the density of labels (or the number of labels) can be used to determine whether the identification (or counting) of overlapping labels is accurate. For example, when the observed fraction of overlapping labels and the observed density (or number) of labels does not follow the relationship illustrated in FIG. 5C, it can be determined that the observed fraction of overlapping labels and/or the observed density (or number) of labels are inaccurate.

Figure 5D:
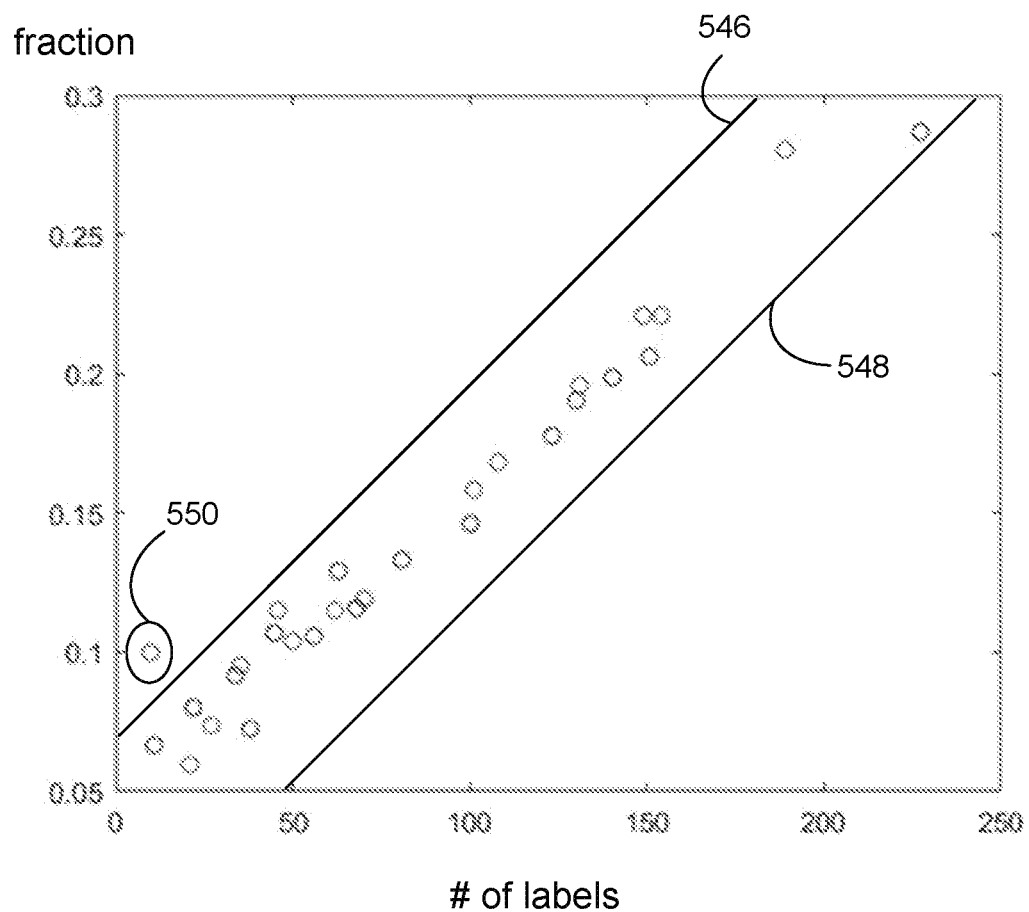
FIG. 5D illustrates a working example of verifying counts of labels in accordance with some embodiments.

FIG. 5D illustrates a working example of verifying counts of labels in accordance with some embodiments.

Shown in FIG. 5D are counts and fractions of overlapping labels for Alexa594 (shown in blue) and Alexa647 (shown in red) dye molecules. Each data point represents a number of labels and a fraction of overlapping labels for corresponding dye molecules in a respective region (or a respective image). FIG. 5D shows that most data points show the linear relationship described above with respect to FIG. 5C. For example, as the number (or density) of labels increases, the fraction of overlapping labels also increases. In some embodiments, upper bound 546 and/or lower bound 548 are used to identify one or more non-conforming data points. For example, data point 550 that is located above upper bound 546 is identified as a non-conforming data point (e.g., an inaccurate determination of overlapping labels and/or a density or number of labels). In some embodiments, one or more non-conforming data points are omitted from determining a total number of labels (e.g., a number of labels represented by a non-conforming data point is replaced by an average number of labels). In some embodiments, upper bound 546 and lower bound 548 are selected based on statistics of data points (e.g., using an average and a standard deviation of data points).

Figure 6B:
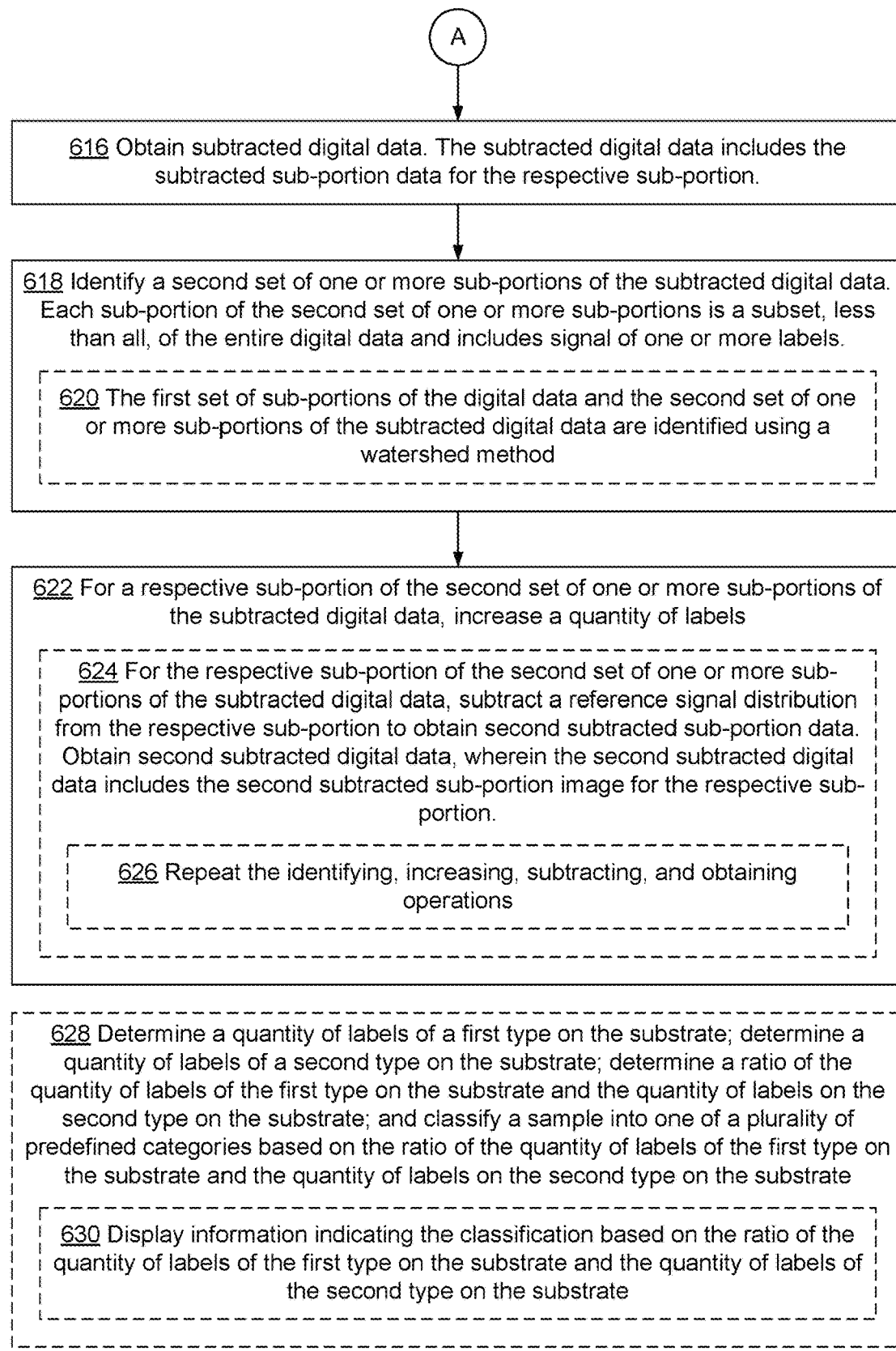

FIGS. 6A-6B are flowcharts representing method 600 of quantifying labels (e.g., signal molecules and/or groups of signal molecules, including optically active dyes, such as fluorescent dyes, nanoparticles, such as fluorospheres and quantum dots, rods or nanobars, and surface plasmon resonant particles (PRPs) or resonance light scattering particles (RLSs)-particles of silver or gold that scatter light (the size and shape of PRP/RLS particles determines the wavelength of scattered light. See Schultz et al., 2000, PNAS 97: 996-1001; Yguerabide, J. and Yguerabide E., 1998, Anal Biochem 262: 137-156) on a substrate in accordance with some embodiments.

Method 600 is particularly useful when the labels are aggregated on a substrate (e.g., when the labels are aggregated in a high density region so that multiple labels are located in a single sub-portion or a single sub-region). In some embodiments, the labels are aggregated due to surface features (e.g., non-uniform distribution of capture probes, uneven surface (e.g., due to surface scratches), drying effects, or other artifacts of manufacturing). Also method 600 is useful when labels are at high density or when the density varies across the substrate leading to regions of high density. Method 600 reduces the need to control the density of labels across the surface, which is difficult to achieve.

Method 600 is performed at an electronic device (e.g., device 300 in FIG. 3) with one or more processors and memory.

The device obtains (602) digital data corresponding to a multi-dimensional (e.g., two-dimensional) measurement over the substrate (e.g., the image shown in FIG. 2). For example, the device obtains the digital data from a camera (e.g., database 354 in FIG. 3A) by initiating the camera to collect multi-dimensional measurement data). Alternatively, the device retrieves the digital data from a storage device that is located locally (e.g., within the device) or remotely (e.g., receiving the digital data through communications networks from a remote data server). In some embodiments, the digital data includes signal of 100 or more labels (e.g., signal molecules). In some embodiments, the digital data includes signal of 1,000 or more labels. In some embodiments, the digital data includes signal of 10,000 or more labels. In some embodiments, the digital data is an image of labels (e.g., fluorophores having two or more colors, such as fluorophores of a first type having a first color and fluorophores of a second type having a second color, immobilized on the substrate). In some embodiments, the device obtains the digital data corresponding to the multi-dimensional measurement over the substrate in response to a user input (e.g., clicking of a button to start collection and/or analysis of multi-dimensional data).

In some embodiments, the digital data includes multiple overlapping images (e.g., images of a same location of the substrate that have been collected sequentially over a period of time). In some embodiments, the digital data includes multiple images that at least partially overlap one another. In some embodiments, the digital data includes multiple non-overlapping images (e.g., images are located adjacent to one another without even a partial overlap). In some embodiments, the digital data includes multiple images that are separate from one another (e.g., a distance between a first area on the substrate that corresponds to a first image of the multiple images and a second area on the substrate that is closest to the first area, among areas corresponding to the images, and corresponds to a second image of the multiple images is greater than a width of the first area).

In some embodiments, the digital data corresponding to the multi-dimensional (e.g., two-dimensional) measurement over the substrate is collected with a super-resolution method. As explained above, one of the challenges in quantifying fluorophores arises when fluorophores exist at high density. This is due to the diffraction limit of light, leading to a blurred image of each fluorophore. When two or more fluorophores are spaced closer than the size of the blurring, then the two fluorophores will appear as a single fluorophore within the image. To accurately count fluorophores at high density, it is useful to increase spatial resolution of a light microscope. In some embodiments, the resolution is increased by using the properties of the fluorophores (e.g. blinking, bleaching or photo-activatable/convertible/switchable probes) in combination with acquiring a long series of images and data processing to obtain a final image of high resolution, known as single-molecule localization microscopy (Patterson, 2010; Huang 2009). In some embodiments, structured light patterns are used to illuminate the samples (for instance, (saturated)-structured-illumination ((S)-SIM) or stimulated emission depletion microscopy (STED) (Gustafsson 2000, Hell 2009, Ta 2015), which increases spatial resolution (Schermelleh 2010). Enhancing the resolution or temporal information of the sample allows more accurate quantification of the number of fluorophores on the sample.

In some embodiments, obtaining the digital data of the substrate includes (604) obtaining digital data of labels on the substrate (e.g., labels on the substrate, as shown in FIG. 1), where the labels are not immersed in a liquid solution. In some embodiments, the digital data of the substrate is obtained from labels on the substrate that is dry. In some embodiments, the digital data (e.g., an image) of the substrate is collected while the substrate (and/or the labels thereon) is at least partially covered with a liquid. For example, water or oil is used to increase a resolving power of an optical microscope (e.g., with a water-immersion or oil-immersion lens). The inventors of this application have discovered that the labels are bleached faster when the labels are immersed in a liquid. The inventors of this application have also discovered that, by obtaining the digital data of the substrate while the substrate (and the labels thereon) are not immersed in a liquid solution (e.g., while the substrate is dry), the photobleaching is reduced, thereby leading to more accurate quantification of labels.

The device identifies (606) a first set of sub-portions of the digital data. Each sub-portion of the first set of sub-portions is a subset, less than all, of the entire digital data and includes signal of one or more labels or one or more groups of labels. For example, as shown in FIG. 4A, regions 405 and 407 are identified from the digital data, and regions 405 and 407 cover less than the entire digital data (e.g., one or more portions of the digital data are not included in the first set of sub-portions). In some embodiments, each sub-portion of the first set of sub-portions corresponds to a single contiguous portion of the digital data. In some embodiments, the entire digital data image includes one or more sub-portions that include no signal of a signal molecule (or a label). In some embodiments, a portion of the digital data that includes no signal of a signal molecule (or a label) is excluded. For example, in some embodiments, the device identifies a plurality of sub-portions of the digital data and identifies sub-portions that include signal of one or more labels (e.g., excludes one or more sub-portions that do not include signal of one or more labels). This eliminates the need for processing the portion of the digital data that includes no signal of a label, which in turn reduces power consumption and saves computing resources.

In some embodiments, the first set of sub-portions includes (608) two or more sub-portions. The two or more sub-portions in the first set of sub-portions are not contiguous. In some embodiments, a first sub-portion of the first set of sub-portions is not contiguous with a second sub-portion of the first set of sub-portions. For example, as shown in FIG. 4A, region 405 and region 407 are not contiguous (e.g., region 407 does not extend from region 405, and there is a gap between region 405 and region 407 that is not covered by any of region 405 and region 407).

For a respective sub-portion of the first set of sub-portions of the digital data, the device increases (610) a quantity of labels, and subtracts a reference signal distribution from the respective sub-portion to obtain subtracted sub-portion data. For example, in FIG. 4A, a count of labels is increased by one, and a reference signal of a single label is subtracted as shown in FIG. 4B. In some embodiments, increasing the quantity includes increasing a count of single molecules by a whole number (e.g., one). In some embodiments, increasing the quantity includes increasing a fraction (e.g., a weighted count, which is optionally based on a probability).

In some embodiments, the device counts the labels based on the digital data. In some embodiments, the counting step comprises determining the numbers of labels (or probes or probe sets coupled with the labels) based on an intensity, energy, relative signal, signal-to-noise, focus, sharpness, size, or shape of one or more labels. In some embodiments, the methods described herein includes the step of enumerating, quantitating, detecting, discovering, determining, measuring, evaluating, calculating, counting, and/or assessing the labels (or probes or probe sets coupled with the labels). This step is not limited to integer counting of the labels, probes, and probe sets. For example, in some cases, counts are weighted by the intensity of the signal from the label. In some embodiments, higher intensity signals are given greater weight and result in a higher counted number compared to lower intensity signals. In the instance where two molecules are very close together (for example, when imaging is diffraction limited), the two labels will not be easily resolved from one another. In this case they may appear to be a single label, but with greater intensity than a typical single label (i.e. the cumulative signal of both the labels). As such, counting can be more accurate when the intensity or other metrics of the label, such as size and shape described below is considered or weighted compared to counting the number of labels in the image without considering these metrics. In some embodiments, the shapes of the labels are considered, and the counting may include or exclude one or more of the labels depending on the shapes of the labels. In additional embodiments, the size of one or more labels or items, objects, or spots on an image may be considered, and the counting may include, exclude, or adjusted depending on the size. In further embodiments, counting may be done on any scale, including but not limited to integers, rational or irrational numbers. Any properties of the label or multiple labels may be used to define the count given to the observation.

In some embodiments, the counting step includes determining the numbers of labels, probes or probe sets by summation over a vector or matrix containing the information (e.g. intensity, energy, relative signal, signal-to-noise, focus, sharpness, size or shape) about the label. For example, for each discrete observation of a label, information on its size, shape, energy, relative signal, signal-to-noise, focus, sharpness, intensity and other factors may be used to weight the count. Certain examples of the value of this approach would be when two fluorophores are coincident and appear as a single point. In this case, two fluorophores would have higher intensity than one fluorophore, and thus this information may be used to correct the count (i.e. counting 2 instead of 1). In some embodiments, the count can be corrected or adjusted by performing the calibrating described below. The vector or matrix may contain integer, rational, irrational or other numeric types. In some embodiments, weighting may also include determining, evaluating, calculating, or assessing likelihoods or probabilities, for example, the probability that an observation is a label, not a background particle. These probabilities may be based on prior observations, theoretical predictions or other factors. In additional embodiments, the initial count is the number of putative labels observed. This number may then be improved, corrected or calibrated by weighting each of the putative labels in the appropriate manner.

In some embodiments, subtracting the reference signal distribution from the respective sub-portion includes (612) identifying a location, within the respective sub-portion, with a peak signal intensity (e.g., via peak intensity detection, Gaussian fitting, finding a centroid, etc.), aligning the reference signal distribution to the location with the peak signal intensity, and subtracting the reference signal distribution, aligned to the location with the peak signal intensity, from the respective sub-portion. For example, as shown in FIG. 4A, a maximum intensity value of intensity profile 402 within region 405 is identified as the location with the peak signal intensity, reference signal 404 is aligned to the location with the peak signal intensity, and aligned reference signal 404 is subtracted from intensity profile 402 as shown in FIG. 4B.

In some embodiments, the reference signal distribution corresponds (614) to a point spread function of a single signal molecule. In some embodiments, the reference signal distribution corresponds to an image of a single signal molecule. In some embodiments, the reference signal distribution represents characteristics of a measurement system (e.g., an optical system) used to measure a signal of the single signal molecule.

In some embodiments, obtaining the digital data of the substrate includes receiving the digital data from another electronic device that is distinct and remote from the electronic device. For example, the device receives the digital data from a remote electronic device (e.g., a client device) through a network using communication interfaces 304 and communications module 320 (FIG. 3A). In some embodiments, obtaining the digital data of the substrate includes retrieving the digital data from a storage device (e.g., a hard drive). For example, the device retrieves the digital data from database 354 (FIG. 3A).

The device obtains (616, FIG. 6B) subtracted digital data. The subtracted digital data includes the subtracted sub-portion data for the respective sub-portion (e.g., adjusted intensity profile 406 in FIG. 4B).

The device identifies (618) a second set of one or more sub-portions of the subtracted digital data (e.g., regions 409 and 411 in FIG. 4B). Each sub-portion of the second set of one or more sub-portions is a subset, less than all, of the entire digital data and includes signal of one or more labels.

In some embodiments, the first set of sub-portions of the digital data and the second set of one or more sub-portions of the subtracted digital data are identified (620) using a watershed method (e.g., by applying the watershed method on a gradient of the digital data).

For a respective sub-portion of the second set of one or more sub-portions of the subtracted digital data, the device increases (622) a quantity of labels (e.g., in FIGS. 4B-4C, the device increases the count of labels once for region 409 and once for region 411, thereby increasing the count of labels by two). In some embodiments, the quantity of labels increased for the respective sub-portion of the second set of one or more sub-portions of the subtracted digital data is the same as the quantity of labels increased for the respective sub-portion of the first set of sub-portions of the digital data (e.g., a total quantity of labels is increased upon a detection of labels in the first set of regions and also upon a subsequent detection of labels in the second set of one or more regions). For example, the quantity of labels is increased for the respective sub-portion of the second set of one or more sub-portions of the subtracted digital data and the quantity of labels is subsequently increased for the respective sub-portion of the first set of sub-portions of the digital data. In some embodiments, the quantity of labels increased for the respective sub-portion of the second set of one or more sub-portions of the subtracted digital data is distinct and separate from the quantity of labels increased for the respective sub-portion of the first set of sub-portions of the digital data. For example, the quantity of labels increased for the respective sub-portion of the second set of one or more sub-portions of the subtracted digital data and the quantity of labels increased for the respective sub-portion of the first set of sub-portions of the digital data are maintained and/or stored separately (e.g., as separate counts). In some embodiments, a sum of the quantity of labels increased for the respective sub-portion of the second set of one or more sub-portions of the subtracted digital data and the quantity of labels increased for the respective sub-portion of the first set of sub-portions of the digital data is used to quantify labels.

In some embodiments, the device subtracts a background (e.g., a global background or a local background). In some embodiments, the background is determined (or estimated) by fitting (e.g., a polynomial fit) and/or averaging.

In some embodiments, for the respective sub-portion of the second set of one or more sub-portions of the subtracted digital data, the device subtracts (624) a reference signal distribution from the respective sub-portion to obtain second subtracted sub-portion data, and obtains second subtracted digital data. The second subtracted digital data includes the second subtracted sub-portion image for the respective sub-portion. For example, in FIG. 4B, reference signal 408 is subtracted from adjusted intensity profile 406 for region 409, and second adjusted intensity profile 410 (shown in FIG. 4C) is obtained.

In some embodiments, the device repeats (626) the identifying, increasing, subtracting, and obtaining operations.

In some embodiments, the device displays the quantity of labels for the respective sub-portion of the second set of one or more sub-portions of the subtracted digital data. In some embodiments, the device displays a total quantity of labels (e.g., a sum of the quantity of labels for respective sub-portions of the second set of one or more sub-portions of the subtracted digital data).

In some embodiments, the device stores the quantity of labels for the respective sub-portion of the second set of one or more sub-portions of the subtracted digital data (e.g., in database 354 in FIG. 3A). In some embodiments, the device stores the total quantity of labels (e.g., in database 354).

In some embodiments, the device determines (628) a quantity of labels of a first type (e.g., a fluorophore having a first color) on the substrate (e.g., using the method described above), and determines a quantity of labels of a second type (e.g., a fluorophore having a second color that is distinct from the first color) that are distinct from labels of the first type. The device determines a ratio of the quantity of labels of the first type on the substrate and the quantity of labels on the second type on the substrate. The device classifies a sample (e.g., a biological fluid a cell lysate, or a liquid containing genomic DNA, etc. that is used with (or analyzed using) probe products) into one of a plurality of predefined categories. For example, a fetus having a trisomy 21 has three copies of chromosome 21 and two copies of chromosome 20 while a mother may have two copies of chromosome 21 and two copies of chromosome 20. Thus, by determining a quantity of labels of a first type (e.g., labels associated with probes configured to bind to chromosome 21) and a quantity of labels of a second type (e.g., labels associated with probes configured to bind to chromosome 20), determining a ratio of the two, and classifies a sample (e.g., a blood sample from the mother) into one of: a normal fetus (e.g., if the ratio of the labels associated with probes configured to bind to chromosome 21 and the labels associated with probes configured to bind to chromosome 20 is 1) or a fetus with trisomy 21 (e.g., if the ratio of the labels associated with probes configured to bind to chromosome 21 and the labels associated with probes configured to bind to chromosome 20 is greater than 1).

In some embodiments, the device displays information indicating the classification based on the ratio of the quantity of labels of the first type on the substrate and the quantity of labels of the second type on the substrate (e.g., a message indicating whether the fetus has trisomy 21 or not). In some embodiments, the device displays the ratio of the quantity of labels of the first type on the substrate and the quantity of labels of the second type on the substrate.

It should be understood that the particular order in which the operations in FIGS. 6A-6B have been described is merely exemplary and is not intended to indicate that the described order is the only order in which the operations could be performed. One of ordinary skill in the art would recognize various ways to reorder the operations described herein. Additionally, it should be noted that details of other processes described herein with respect to method 600 are also applicable in an analogous manner to method 700 described below with respect to FIGS. 7A-7B. For example, method 700 optionally includes obtaining digital data corresponding to a multi-dimensional measurement (e.g., multi-dimensional measurements, such as two-dimensional measurements, in a time-series) as described above with respect to method 600. For brevity, these details are not repeated here.

Method 700 is particularly useful when an integration time is sufficiently long so that the labels bleach or blink during the integration time (or data acquisition).

FIGS. 7A-7B are flowcharts representing method 700 of quantifying labels in accordance with some embodiments. Method 700 is performed at an electronic device (e.g., device 300 in FIG. 3) with one or more processors and memory.

The device obtains (702) digital data representing a series of intensity values of one or more labels within a particular region over a period of time (e.g., time-series data 358 in FIG. 3A). The series of intensity values of one or more labels includes intensity values of the one or more labels at respective time frames within the period of time (e.g., intensity plot 502 in FIG. 5A). In some embodiments, the respective time frames correspond to a same time interval (e.g., (beginning of) each time frame is separated by 1 second). In some embodiments, the respective time frames correspond to different time intervals (e.g., the respective time frames include a first time frame that is separated by 1 second from a preceding time frame and a second time frame that is separated by 0.1 second from a preceding time frame). In some embodiments, the respective time frames correspond to the same time duration (e.g., each time frame corresponds to 1 second integration time). In some embodiments, the respective time frames correspond to different time durations (e.g., the respective time frames include a first time frame that corresponds to 1 second integration time and a second time frame that corresponds to 0.1 second integration time).

The series of intensity values of one or more labels includes a first group of intensity values that is represented by a first intensity value (e.g., intensity values 506 having an average value 1 in FIG. 5A) and a second group of intensity values that is represented by a second intensity value that is distinct from the first intensity value (e.g., intensity values 508 having an average value 0.1 in FIG. 5A). In some embodiments, the second intensity value is less than the first intensity value. In some embodiments, the second group of intensity values does not overlap with the first group of intensity values (e.g., as shown in histogram 504 in FIG. 5A, the second group of intensity values represented by bins 512 do not overlap with the first group of intensity values represented by bins 510). In some embodiments, the first group of intensity values does not include any intensity value of the second group of intensity values, and the second group of intensity values does not include any intensity value of the first group of intensity values. In some embodiments, the second group of intensity values at least partially overlaps with the first group of intensity values.

In some embodiments, the first group of intensity values corresponds (704) to a first range of intensity values. The second group of intensity values corresponds to a second range of intensity values that does not overlap with the first range of intensity values (e.g., as shown in histogram 504 in FIG. 5A, the range of the second group of intensity values represented by bins 512 do not overlap with the range of the first group of intensity values represented by bins 510).

In some embodiments, the first intensity value is (706) an average of the first group of intensity values. The second intensity value is an average of the second group of intensity values.

In some embodiments, the first intensity value is a median of the first group of intensity values; and the second intensity value is a median of the second group of intensity values. In some embodiments, the first intensity value is a maximum value of the first group of intensity values; and the second intensity value is a maximum value of the second group of intensity values. In some embodiments, the first intensity value is a minimum value of the first group of intensity values; and the second intensity value is a minimum value of the second group of intensity values.

The device determines (708) the first intensity value and the second intensity value from the digital data. For example, the device groups the intensity values in the digital data (e.g., time-series data) and determines a representative intensity value for each group.

In some embodiments, determining the first intensity value and the second intensity value includes (710) separating the series of intensity values into at least the first group of intensity values and the second group of intensity values (e.g., based on the standard deviation of each group).

In some embodiments, the device replaces (712) the second group of intensity values with the first intensity value. For example, as shown in FIG. 5A, the device replaces reduced intensity values 508 (e.g., due to photobleaching and/or blinking) with a representative intensity value of non-reduced intensity values, which facilitates more accurate quantification of labels.

The device quantifies (714) a number of the one or more labels, represented by the digital data, based on at least the first intensity value. For example, the second intensity value, which represents reduced intensity values, is ignored in quantifying the number of the one or more labels. In some embodiments, the device quantifies the number of the one or more labels based on a profile of the one or more labels (e.g., a shape of a label in a spatial domain, such as symmetry; an intensity of a signal from a label; a wavelength of light emitted by a label, such as a peak wavelength and/or a peak shape in the wavelength domain, etc.).

In some embodiments, quantifying the number of the one or more labels includes (716) quantifying the number of the one or more labels based on at least the first intensity value and another intensity value. In some embodiments, the another intensity value is the second intensity value. In some embodiments, the another intensity value is one of the series of intensity values other than the first intensity value. In some embodiments, the another intensity value is a representative intensity value (e.g., an average or a median) of at least a portion of the series of intensity values. In some embodiments, the another intensity value is a background intensity value.

In some embodiments, the device obtains (718) a series of adjusted intensity values by subtracting the second intensity value from the series of intensity values (e.g., the second intensity value is used as a background intensity value). Quantifying the number of the one or more labels includes quantifying the number of the one or more labels based on the series of adjusted intensity values. In some embodiments, the device obtains the series of adjusted intensity values by subtracting from the series of intensity values a lesser value between the first intensity value and the second intensity value. For example, an intensity value between the first intensity value and the second intensity value is selected as a background intensity value.

In some embodiments, the device determines (720) a total intensity value from the series of intensity values, and quantifies the number of the one or more labels based on at least the total intensity value (e.g., area 505 in FIG. 5A is used to determine the number of the one or more labels). In some embodiments, the total intensity value is determined using the first intensity value (e.g., the first intensity value multiplied by a number of time frames). In some embodiments, the total intensity value is determined using the series of adjusted intensity values (e.g., a sum of the series of adjusted intensity values). In some embodiments, the total intensity value is determined using the replaced intensity values (e.g., area 507 in FIG. 5A is used to determine the number of the one or more labels). In some embodiments, the device determines the total intensity value from the series of intensity values, adjusts the total intensity value (e.g., scaling the total intensity by a fraction of time intensity values represented by the first intensity value were observed, such as scaling the total intensity by dividing with 0.7 when intensity values represented by the first intensity value were observed in seven frames out of ten frames), and quantifies the number of the one or more labels based on at least the adjusted total intensity value.

In some embodiments, the device quantifies (722) the number of the one or more labels as one based on a determination that the series of intensity values consist of the first group of intensity values and the second group of intensity values (e.g., any intensity value in the series of intensity values belongs to either the first group of intensity values or the second group of intensity values). For example, intensity plot 502 in FIG. 5A shows a pattern of a single label that has been bleached during the measurement period. Thus, based on a determination that the intensity values in intensity plot 502 belong to either the first group of intensity values 506 or the second group of intensity values 508 only, the number of labels is determined (or estimated) to be one.

In some embodiments, the series of intensity values of one or more labels also includes (724) a third group of intensity values that is represented by a third intensity value that is distinct from the first intensity value and the second intensity value. The device quantifies the number of the one or more labels as two based on a determination that the series of intensity values consist of the first group of intensity values, the second group of intensity values, and the third group of intensity values (e.g., any intensity value in the series of intensity values belongs to one of: the first group of intensity values, the second group of intensity values, and the third group of intensity values). For example, intensity plot 522 in FIG. 5B shows a pattern of two labels that have been bleached during the measurement period. Thus, based on a determination that the intensity values in intensity plot 522 belong to one of the first group of intensity values 526, the second group of intensity values 528, and the third group of intensity values 530, the number of labels is determined (or estimated) to be two.

In some embodiments, the series of intensity values of one or more labels also includes (726) one or more additional groups of intensity values, each group of intensity values represented by a respective intensity value that is distinct from any intensity value that represents any other group of intensity values. The device quantifies the number of the one or more labels based on a determination that the series of intensity values consist of the first group of intensity values, the second group of intensity values, the third group of intensity values, and the one or more additional groups of intensity values. For example, if the intensity values are classified into four groups, the number of labels is determined (or estimated) to be three.

In some embodiments, a minimum intensity value of the series of intensity values is selected as a background intensity value.

In some embodiments, the device displays the number of labels. In some embodiments, the device stores the number of labels (e.g., in database 354 in FIG. 3A).

In accordance with some embodiments, a method includes obtaining intensity of one or more labels in multiple frames over a period of time until all of the one or more labels are bleached (e.g., by photobleaching). In some embodiments, a minimum intensity of the one or more labels in the multiple frames is used as a background intensity value.

It should be understood that the particular order in which the operations in FIGS. 7A-7B have been described is merely exemplary and is not intended to indicate that the described order is the only order in which the operations could be performed. One of ordinary skill in the art would recognize various ways to reorder the operations described herein. Additionally, it should be noted that details of other processes described herein with respect to method 700 are also applicable in an analogous manner to method 600 described above with respect to FIGS. 6A-6B. For example, method 600 optionally includes background subtraction based on a first intensity value and/or a second intensity value determined in accordance with method 700. For brevity, these details are not repeated here.

The foregoing description, for purpose of explanation, has been described with reference to specific embodiments. However, the illustrative discussions above are not intended to be exhaustive or to limit the scope of claims to the precise forms disclosed. Many modifications and variations are possible in view of the above teachings.

For example, method 600 and method 700 can be combined to utilize both spatial information and temporal information of labels for quantifying the labels. In accordance with some embodiments, a method for quantifying labels includes obtaining digital data corresponding to multi-dimensional measurements over a substrate, including a series of intensity values of multiple labels at respective locations over a period of time. The method also includes identifying sub-portions of the digital data, where each sub-portion of the sub-portions includes signal of one or more labels. The method further includes comparing for a particular location on a substrate a quantity of labels obtained by method 600 and a quantity of labels obtained by method 700. In some embodiments, a larger value of the quantity of labels obtained by method 600 and the quantity of labels obtained by method 700 is used as a quantity of labels for the particular location on the substrate. In some embodiments, a smaller value of the quantity of labels obtained by method 600 and the quantity of labels obtained by method 700 is used as the quantity of labels for the particular location on the substrate. In some embodiments, an average of the quantity of labels obtained by method 600 and the quantity of labels obtained by method 700 is used as a quantity of labels for the particular location on the substrate. In some embodiments, a median of the quantity of labels obtained by method 600 and the quantity of labels obtained by method 700 is used as a quantity of labels for the particular location on the substrate.

In another aspect, the methods for quantifying labels, described herein, are used in methods of detecting a genetic variation, for example, including the methods described in U.S. Pat. No. 9,212,394, which is incorporated by reference herein in its entirety. For example, the methods for quantifying labels, described herein, are used in diagnosing or detecting a genetic variation including, but not limited to, prenatal diagnosis or cancer diagnosis. The methods include obtaining digital data corresponding to a multi-dimensional (e.g., two-dimensional) measurement over a substrate. In some embodiments, probe products may be hybridized, bound or associated with at least a portion of nucleic acid molecules present in a sample to form probe-target molecule complexes. The sample may be from a pregnant subject or a cancer patient. In additional embodiments, at least a portion of the probe products is immobilized on the substrate with or without the nucleic acid molecules from the sample, and/or at least a portion of the nucleic acid molecules from the sample is immobilized on the substrate before or after forming the probe-target complexes. In further embodiments, a number of probe products representing a number of nucleic acid molecules present in the sample are immobilized on the substrate. In yet further embodiments, the probe products and/or the nucleic acid molecules from the sample may be labeled with any label described herein. By the methods for quantifying labels described herein, a frequency of the nucleic acid molecules from the sample may be quantified. The methods optionally include determining relative numbers of different nucleic acid molecules from the sample and/or from a different subject (e.g. control subject without cancer) by comparing numbers of at least two different labels for different probe products, probe-target molecule complexes or assay products. In some embodiments, a plurality of probe products may be contacted with target molecules to form probe-target molecule complexes in a solution, where the probe products and/or probe-target molecule complexes are labeled directly or indirectly with at least two different labels, and the solution comprising the probe products and/or probe-target molecule complexes may be applied to a solid phase before or after the contacting.

For example, this application is related to method of detecting a genetic variation in a genetic sample from a subject, comprising contacting first and second probe sets to the genetic sample, wherein the first probe set comprises a first labeling probe and a first tagging probe, and the second probe set comprises a second labeling probe and a second tagging probe; hybridizing at least parts of the first and second probe sets to first and second nucleic acid regions of interest in nucleotide molecules of the genetic sample, respectively; ligating the first probe set at least by ligating the first labeling probe and the first tagging probe; ligating the second probe set at least by ligating the second labeling probe and the second tagging probe; optionally amplifying the ligated probe sets; immobilizing the tagging probes to a pre-determined location on a substrate, wherein the first and second labeling probes and/or the amplified labeling probes thereof ligated to the immobilized tagging probes comprise first and second labels, respectively, the first and second labels are different; the immobilized labels are optically resolvable, the immobilized first and second tagging probes and/or the amplified tagging probes thereof comprise first and second tags, respectively, and the immobilizing step is performed by immobilizing the tags to the predetermined location; counting (i) a first number of the first label immobilized to the substrate, and (ii) a second number of the second label immobilized to the substrate, the counting at least comprising quantifying the first and second labels according to the method of any one of claims 1-19; and comparing the first and second numbers to determine the genetic variation in the genetic sample. In some embodiments, the subject is a pregnant subject, and the genetic variation is a genetic variation in the fetus of the pregnant subject. In further embodiments, the counting and/or comparing steps described herein may be performed by digital image processing. The "digital image" may include a collection of image data in any format, capable of being stored or retained in an electronic form.

The embodiments were chosen and described in order to best explain the principles of the various described embodiments and their practical applications, to thereby enable others skilled in the art to best utilize the invention and the various described embodiments with various modifications as are suited to the particular use contemplated.

APPENDIX

```
//// Image Pre-processing
//      (Optional) Cropping
//      Crop data such that the remaining data is from a region that is uniformly illuminated on
        the microscope.
crop_RawData = crop(RawImage(s))
// If data contains multiple time points, sum the data across time
crop_RawImage = sum(cropRawData, time)
// (Optional) Background Subtraction
// Find median of cropped data
medianLevel = median(crop_RawImage)
// Remove intensities that are larger than the median value
Bgnd2fit = crop_RawImage(crop_RawImage < medianLevel)
// Use a polynomial fit to determine the background level and subtract this from the cropped Data
BkSubImage = crop_RawImage – fit(Bgnd2fit)
// (Optional) If present, remove data with anomalous intensities from background subtracted data
        (removes large aggregates or dirt that are not "fluorophore-like" from the final count)
BkSubImageClean = removeJunk(BkSubImage)
/// Counting
// Count is initially equally to zero
Count = 0
// For Do the following steps for a user-defined number of iterations (N)
For (i=0; i< N; i++)
        // Watershed the background subtracted data
        watershedRegions = watershed(BkSubImageClean)
        // Find maximum intensity of each region watershed domain and the position of the
        maximum intensity
        fluorophoreProperties = maxIntensity(watershedRegions)
        // Watershed domains with fluorophore properties different than expected from a single
            fluorophore are flagged and counted
        Fluorophores2subtract = findUnexpectedProperties(fluorophoreProperties)
        Count = Count + Fluorophores2subtract
        // Subtract the "non-single" fluorophores from the background subtracted image
        Image2rewatershed = BkSubImageClean – Fluorophores2subtract
        BkSubImageClean = Image2rewatershed
Count = Count + number of fluorophoreProperties
```

What is claimed is:

1. A method of counting individual optically active dye labels immobilized on a substrate, the method comprising:
at an electronic device with one or more processors and memory:
(a) obtaining digital image data corresponding to a two-dimensional digital image of the substrate,
wherein the digital image data comprise a two-dimensional array of intensity values, where each intensity value corresponds to a particular location on the substrate;
(b) identifying a set of regions of the digital image data by segmenting the digital image data into multiple regions based on the intensity values and the particular locations on the substrate,
wherein each region comprises an average, median, or maximum intensity value which is above a predefined threshold;
(c) for each region of the digital image data:
increasing a count of optically active dye labels by one; and
identifying a peak location of intensity values from an optically active dye label, and subtracting a reference signal distribution from the intensity values at the identified peak location to obtain adjusted intensity values for the region, wherein the reference signal distribution corresponds to a point spread function of a single optically active dye label;
(d) identifying a first set of one or more sub-regions of the adjusted intensity values for each of said regions by segmenting the adjusted intensity values for each of said regions into one or more sub-regions based on the adjusted intensity values and the particular locations on the substrate,
wherein, if the average, median, or maximum adjusted intensity value in any of said sub-regions is above the predefined threshold,
for each of said sub-regions:
increasing the count of the optically active dye labels by one.

2. The method of claim 1, wherein the digital image data is segmented into multiple regions using a watershed method.

3. The method of claim 1, wherein the digital image data is segmented into multiple regions using a Minimum Spanning Forest method.

4. The method of claim 1, wherein the peak location of intensity values is identified as one of a centroid of the region, or a maximum intensity value of the intensity values, or is identified by fitting the intensity values with a profile of a reference signal.

5. The method of claim 1, wherein, for each of the sub-regions having an average, median, or maximum adjusted intensity value above a predetermined threshold:
identifying a peak location of adjusted intensity values from an optically active dye label, and subtracting a reference signal distribution from the adjusted intensity values at the identified peak location to obtain second adjusted intensity values for the sub-region, wherein the reference signal distribution corresponds to a point spread function of a single optically active dye label;
identifying a second set of one or more second sub-regions of the second adjusted intensity values for each of said sub-regions by segmenting the second adjusted intensity values for each of said sub-regions into one or more second sub-regions based on the second adjusted intensity values and the particular locations on the substrate,
wherein, if the average, median, or maximum second adjusted intensity value in any of said second sub-regions is above the predefined threshold,
for each of said second sub-regions:
increasing the count of the optically active dye labels by one.

6. The method of claim 1, wherein steps (b) to (d) repeated until the average, median, or maximum intensity of an adjusted intensity profile is less than the predefined threshold.

7. The method of claim 1, wherein the digital image data includes digital data of optically active dye labels on the substrate, wherein the optically active dye labels are not immersed in a liquid solution.

8. The method of claim 1, wherein, in step (a), the digital image data is obtained from a first electronic device, which is distinct and remote from a second electronic device performing steps (b) to (d).

9. The method of claim 1, wherein, in step (a), obtaining the digital image data comprises retrieving the digital image data from a storage device, optionally wherein the digital image data is retrieved from a database.

10. An electronic device, comprising:
one or more processors; and
memory storing one or more programs for execution by the one or more processors, the one or more programs including instructions for performing the method of claim 1.

11. A computer readable storage medium, storing one or more programs for execution by one or more processors of an electronic device, the one or more programs including instructions for performing the method of claim 1.

12. The computer readable storage medium of claim 11, wherein the computer readable storage medium includes a non-transitory computer readable storage medium.

13. A method of detecting a genetic variation in a genetic sample from a subject, comprising
contacting first and second probe sets to the genetic sample, wherein the first probe set comprises a first labeling probe and a first tagging probe, and the second probe set comprises a second labeling probe and a second tagging probe,
hybridizing at least parts of the first and second probe sets to first and second nucleic acid regions of interest in nucleotide molecules of the genetic sample, respectively,
ligating the first probe set at least by ligating the first labeling probe and the first tagging probe,
ligating the second probe set at least by ligating the second labeling probe and the second tagging probe,
optionally amplifying the ligated probe sets,
immobilizing the tagging probes to a pre-determined location on a substrate, wherein
the first and second labeling probes and/or the amplified labeling probes thereof ligated to the immobilized tagging probes comprise first and second labels, respectively,
the first and second labels are different,
the immobilized labels are optically resolvable,
the immobilized first and second tagging probes and/or the amplified tagging probes thereof comprise first and second tags, respectively, and
the immobilizing step is performed by immobilizing the tags to the predetermined location, counting (i) a first number of the first label immobilized to the substrate, and (ii) a second number of the second label immobilized to the substrate, the counting at least comprising quantifying the first and second labels according to the method of claim 1, and comparing the first and second numbers to determine the genetic variation in the genetic sample.

14. The method of claim 13, wherein the subject is a pregnant subject, and the genetic variation is a genetic variation in the fetus of the pregnant subject.

* * * * *